US008440460B2

(12) United States Patent
Estrov et al.

(10) Patent No.: US 8,440,460 B2
(45) Date of Patent: May 14, 2013

(54) METHODS FOR TRANSDIFFERENTIATING CELLS

(75) Inventors: Zeev Estrov, Houston, TX (US); Gideon Strassmann, Naples, FL (US)

(73) Assignees: The Board of Regents of the University of Texas System, Austin, TX (US); Gideon Strassmann, Ramat Gan (IL)

( * ) Notice: Subject to any disclaimer, the term of this patent is extended or adjusted under 35 U.S.C. 154(b) by 837 days.

(21) Appl. No.: 11/996,732

(22) PCT Filed: Jul. 24, 2006

(86) PCT No.: PCT/US2006/028701
§ 371 (c)(1),
(2), (4) Date: Apr. 9, 2010

(87) PCT Pub. No.: WO2007/016037
PCT Pub. Date: Feb. 8, 2007

(65) Prior Publication Data
US 2011/0206644 A1    Aug. 25, 2011

Related U.S. Application Data

(60) Provisional application No. 60/702,749, filed on Jul. 27, 2005, provisional application No. 60/729,708, filed on Oct. 24, 2005, provisional application No. 60/734,864, filed on Nov. 9, 2005.

(51) Int. Cl.
*C12N 5/00* (2006.01)

(52) U.S. Cl.
USPC ........... 435/377; 435/325; 435/375; 424/93.7

(58) Field of Classification Search ........................ None
See application file for complete search history.

(56) References Cited

U.S. PATENT DOCUMENTS

| | | | | |
|---|---|---|---|---|
| 5,306,305 | A * | 4/1994 | Lee ................................. | 435/325 |
| 5,736,396 | A * | 4/1998 | Bruder et al. .................. | 435/366 |
| 6,087,168 | A | 7/2000 | Levesque et al. .............. | 435/455 |
| 7,112,440 | B2 | 9/2006 | Abuljadayel ................... | 435/325 |
| 7,129,086 | B2 | 10/2006 | Torok-Storb et al. .......... | 435/325 |
| 2003/0049649 | A1 | 3/2003 | Wolffe et al. .................. | 435/455 |
| 2003/0211603 | A1 | 11/2003 | Earp et al. ...................... | 800/10 |
| 2005/0042687 | A1 | 2/2005 | Kelly et al. ...................... | 435/7.2 |
| 2005/0276793 | A1 | 12/2005 | Milhem et al. ............. | 424/93.21 |

FOREIGN PATENT DOCUMENTS

| | | |
|---|---|---|
| EP | 1 366 773 A1 | 12/2003 |
| WO | WO 00/05419 | 2/2000 |
| WO | WO 2004/045517 | 6/2004 |

OTHER PUBLICATIONS

Vanderslice et al. "Anti-tumor surveillance of non-contact-inhibited transformed cell lines", Int. J. Cancer, 1988, 42:460-463.*
Tosh D et al. 2002. Conversion of pancreatic cells to hepatocytes. Biochem Soc Trans 30: 51-55.*
Kim J et al. 2011. Direct reprogramming of mouse fibroblasts to neural progenitors. Proc Natl Acad Sci USA 108: 7838-7843.*
Reinecke H et al. 2002. Skeletal muscle stem cells do not transdifferentiate into cardiomyocytes after cardiac grafting. J Mol Cell Cardiol 34: 241-249.*
Murry CE et al. 2004. Haematopoietic stem cells do not transdifferentiate into cardiac myocytes in myocardial infarcts. Nature 428: 664-668.*
Deng J et al. 2003. Neural transdifferentiation potential of hepatic oval cells in the neonatal mouse brain. Exp Neurol 182: 373-382.*
Holden C et al. 2002. Plasticity: Time for a reappraisal? Science 296: 2126-2129.*
Takahashi K et al. 2007. Induction of pluripotent stem cells from adult human fibroblasts by defined factors. Cell 131: 861-872.*
Angoulvant et al., "Human mesenchymal stem cells suppress induction of cytotoxic response to alloantigens," *Biorheology*, 41 (3-4): 469-476, 2004.
Anker et al., "Isolation of mesenchymal stem cells of fetal or maternal origin from human placenta," *Stem Cells*, 22 (7): 1338-1345, 2004.
Austin et al., "A role for the Wnt gene family in hematopoiesis: expansion of multilineage progenitor cells," *Blood*, 89 (10): 3624-3635, 1997.
Bartsch, Jr. et al., "Propagation, expansion, and multilineage differentiation of human somatic stem cells from dermal progenitors," *Stem Cells*, 14 (3): 337-348, 2005.
Boyd and Schrader, "Derivation of macrophage-like lines from the pre-B lymphoma ABLS 8.1 using 5-azacytidine," *Nature*, 297 (5868): 691-693, 1982.
Colter et al., "Rapid expansion of recycling stem cells in cultures of plastic-adherent cells from human bone marrow," *PNAS USA* 20: 7294-7299, 2000.
Devine et al., "Mesenchymal stem cells distribute to a wide range of tissues following systemic infusion into nonhuman primates," *Blood*, 101 (8): 2999-3001, 2003.
Dexter et al., "Haemopoietic stem cells and the problem of self-renewal," *Blood Cells*, 10: 315-339, 1984.
Egger et al., "Epigenetics in human disease and prospects for epigenetic therapy," *Nature*, 429 (6990): 457-463, 2004.

(Continued)

*Primary Examiner* — Lora E Barnhart Driscoll
(74) *Attorney, Agent, or Firm* — Parker Highlander PLLC

(57) ABSTRACT

The present provides methods for affecting and/or altering the differentiation state of a cell. In certain embodiments, the present invention provides methods to transdifferentiate a cell into an endothelial cell or a hematopoietic cell. In the practice of the invention, a demethylating agent (e.g., 5-azacytidine) is used to affect and/or alter the differentiation state of a cell. The invention demonstrates the transdifferentiation of numerous cell types, including cell populations that are themselves somewhat differentiated (e.g., normal fibroblasts) into distinct cell types, including hematopoietic cells and endothelial cells, which transdifferentiation is effected further through the selection of particular growth factors which, together with the demethylating agents, directs the differentiation path. The invention provides a novel approach to providing useful cell types for many types of medical applications.

7 Claims, 14 Drawing Sheets

OTHER PUBLICATIONS

Fernandes et al., "A dermal niche for multipotent adult skin-derived precursor cells," *Nat. Cell Biol.*, 6: 1082-1093, 2004.

Friedenstein et al., "Fibroblast precursors in normal and irradiated mouse hematopoietic organs," *Exp. Hematol.*, 4 (5): 267-274, 1976.

Friedenstein et al., "Stromal cells responsible for transferring the microenvironment of the meopoietic tissues. Cloning in vitro and retransplantation in vivo," *Transplantation*, 17 (4): 331-340, 1974.

Gregory et al., "Wnt signaling inhibitor Dkk-1 is required for re-entry into the cell cycle of human adult stem cells from bone marrow stroma (hMSCs)," *J. Biol. Chem.*, 278: 28067-28078, 2003.

Hennessy et al., "Circulating stem cells and tissue repair," *Panminerva Med.*, 46 (1): 1-11, 2004.

Horwitz et al., "Clinical responses to bone marrow transplantation in children with severe osteogenesis imperfecta," *Blood*, 97: 1227-1231, 2001.

Horwitz et al., "Isolated allogeneic bone marrow-derived mesenchymal cells engraft and stimulate growth in children with osteogenesis imperfecta: implications for cell therapy of bone," *PNAS USA*, 99: 8932-8937, 2002.

Horwitz et al., "Transplantability and therapeutic effects of bone marrow-derived mesenchymal cells in children with osteogenesis imperfecta," *Nat. Med.*, 5: 309-313, 1999.

International Search Report and Written Opinion, issued in Int. App. No. PCT/US2006/28701, mailed Apr. 24, 2007.

Issa, "CpG island methylator phenotype in cancer," *Nat. Rev. Cancer*, 4 (12): 988-993, 2004.

Issa, "Decitabine," *Curr. Opin. Oncol.*, 15 (6): 446-451, 2003.

Jiang et al., "Multipotent progenitor cells can be isolated from postnatal murine bone marrow, muscle, and brain," *Exp. Hematol.*, 30 (8): 896-904, 2002.

Jiang et al., "Neuroectodermal differentiation from mouse multipotent adult progenitor cells," *PNAS USA*, 100 (Supp. 1), 118554-118560, 2003.

Jiang et al., "Pluripotency of mesenchymal stem cells derived from adult marrow," *Nature*, 418 (6893): 41-49, 2002.

Kee and Murre, "Induction of early B cell factor (EBF) and multiple B lineage genes by the basic helix-loop-helix transcription factor E12," *J. Exp. Med.*, 188 (4): 699-713, 1998.

Klinken et al., "Hemopoietic lineage switch: v-raf oncogene converts Emu-myc transgenic B cells into macrophages," *Cell*, 53 (6): 857, 1988.

Koc et al., "Allogeneic mesenchymal stem cell infusion for treatment of metachromatic leukodystrophy (MLD) and Hurler syndrome (MPS-IH)," *Bone Marrow Transplant*, 30 (4): 215-222, 2002.

Körbling and Estrov, "Adult stem cells for tissue repair—a new therapeutic concept?" *N. E. J. Med.*, 349: 570-582, 2003.

Le Blanc et al., "HLA expression and immunologic properties of differentiated and undifferentiated mesenchymal stem cells," *Exp. Hematol.*, 31 (10): 890-896, 2003.

Le Blanc, "Immunomodulatory effects of fetal and adult mesenchymal stem cells," *Cytotherapy*, 5 (6): 485-489, 2003.

Lee et al., "Mesenchymal stem cells from cryopreserved human umbilical cord blood," *Biochem. Biophys. Res. Commun.*, 320: 273-278, 2004.

Milhem et al., "Modification of hematopoietic stem cell fate by 5aza 2'deoxycytidine and trichostatin A," *Blood*, 103 (11): 4102-4110, 2004.

Miura et al., "SHED: stem cells from human exfoliated deciduous teeth," *PNAS USA*, 100 (10): 5807-5812, 2003.

Olmsted-Davis et al., "Primitive adult hematopoietic stem cells can function as osteoblast precursors," *PNAS USA*, 100 (26): 15877-15882, 2003.

Pereira et al., "Cultures of adherent cells from marrow can serve as long-lasting precursor cells for bone, cartilage and lung in irradiated mice," *PNAS USA*, 92: 4857-4861, 1995.

Pittenger et al., "Multilineage potential of adult human mesenchymal stem cells," *Science*, 284 (5411): 143-147, 1999.

Rawadi et al., "BMP2 controls alkaline phosphatase expression and osteoblast mineralization by a Wnt autocrine loop," *J. Bone Min. Res.*, 18: 1842-1853, 2003.

Reyes and Verfaillie, "Characterization of multipotent adult progenitor cells, a subpopulation of mesenchymal stem cells," *Ann. NY Acad. Sci.*, 938: 231-233, 2001.

Santini et al., "Changes in DNA methylation in neoplasiapathophysiology and therapeutic implications," *Ann. Intern. Med.*, 134 (7): 573-586, 2001.

Sekiya et al., "Expansion of human adult stem cells from bone marrow stroma: conditions that maximize yields of early progenitors and evaluate their quality," *Stem Cells*, 20 (6): 530-541, 2002.

Sekiya et al., "In vitro cartilage formation by human adult stem cells from bone marrow stroma defines the sequences of cellular and molecular events during chondrogenesis," *PNAS USA*, 49: 4397-4402, 2002.

Toma et al., "Isolation and characterization of multipotent skin-derived precursors from human skin," *Stem Cells*, 23 (6): 727-737, 2005.

Toma et al., "Isolation of multipotent adult stem cells from the dermis of mammalian skin," *Nat. Cell. Biol.*, 3 (9): 778-784, 2001.

Van Den Berg et al., "Role of members of the WNT gene family in human hemtopoiesis," *Blood*, 92: 3189-3202, 1998.

Willert et al., "Wnt proteins are lipid-modified and can act as stem cell growth factors," *Nature*, 423 (6938): 448-452, 2003.

Xie et al., "Stepwise reprogramming of B cells into macrophages," *Cell*, 117 (5): 663, 2004.

Yen et al., "Isolation of multipotent cells from human term placenta," *Stem Cells*, 23 (1): 3-9, 2005.

Zuk et al., "Human adipose tissue is a source of multipotent stem cells," *Mol. Biol. Cell.*, 13 (12): 4279-4295, 2002.

* cited by examiner

A. Untreated HS-5 cells grown in liquid culture
B. Untreated HS-5 cells plated in methylcellulose
C. 5-azacytidine- and growth factor-treated HS-5 cells cultured in methylcellulose % of CD45-Positive Cells

| Sample | Control | Growth Factors | AZA | AZA + GF |
|---|---|---|---|---|
| Normal #1 | 0 | 0 | 4.08 | 13.27 |
| Normal #2 | 0 | 1.25 | 7.91 | 16.03 |
| Normal #2 | 0 | 2.95 | 1.43 | 7.85 |
| Normal #3 | 0 | 2.9 | 5.41 | 12.88 |

FIG. 7

HLA-ABC immunostaining of NOD/SCID mouse bone marrow 3 weeks after irradiation (30 Gy) and I.V. injection of $10^6$ untreated and treated HS-5 cells HLA-ABC immunostaining of NOD/SCID mouse bone marrow cells 3 weeks after irradiation (30 Gy) and I.V. injection of $10^6$ marrow cells from NOD/SCID mice tranplanted 3 weeks earlier with untreated and treated HS-5 cells

METHODS FOR TRANSDIFFERENTIATING CELLS

Reference is made to priority applications U.S. Provisional Application 60/702,749, filed Jul. 27, 2005; U.S. Provisional Application 60/729,708, filed Oct. 24, 2005; and U.S. Provisional 60/734,864, filed Nov. 9, 2005, all of which are incorporated by reference herein without disclaimer.

BACKGROUND OF THE INVENTION

1. Field of the Invention

The present invention relates generally to the fields of molecular biology. More particularly, it concerns methods for affecting and/or altering the differentiation state of a cell. In certain embodiments, the present invention provides a method to transdifferentiate a cell such as fibroblast or a fibroblast like cell, into a vascular endothelial cell, hematopoietic cell, bone marrow-derived fibroblastic cells, T cells, cells of the granulocyte and monocyte lineage and B cells.

2. Description of the Related Art

Approximately 30 percent of patients who require hematopoietic stem cell transplantation will identify a suitably matched unrelated donor through the National Marrow Donor Program. However, the patient's disease may progress and worsen during the approximately 2 months required to identify an acceptably matched unrelated donor and obtain the graft. This time period would reduce or eliminate the chance of success. In other words, during this waiting period some patients will succumb to the disease and, in many others, the disease will progress to a state at which the patients will not be eligible to undergo hematopoietic stem cell transplantation. For those individuals who require an urgent hematopoietic transplant (most patients) and others for whom an unrelated donor search is unsuccessful, the rapid availability of a partially matched umbilical cord blood (UCB) unit from a volunteer donor cord blood bank has been suggested to offer an alternative treatment option. It has been estimated that approximately 7200 allogeneic hematopoietic transplants were performed in the United States during 2002, and nearly double that number were performed worldwide. More than 200,000 UCB units are available to the public from cord blood banks (1), and more than 3,500 unrelated donor hematopoietic transplants have been performed with UCB; UCB grafts represented a significant and growing fraction of the sources of all hematopoietic grafts employed for pediatric patients in the year 2002 (approximately 15%) (Source: National Marrow Donor Program, Minneapolis (Minn.)).

There are, however, controversies surrounding the role of UCB grafts in hematopoietic transplantation and several disadvantages have been identified. Those include 1) the relative paucity of progenitor cells available (the minimal acceptable cell dose for single unit UCB for adults varies, but is typically at least $1.5 \times 10^7$ to $2.0 \times 10^7$ per kg, and some studies have suggested that a higher minimal doses is needed), 2) prolonged time of neutrophil and platelet engraftment, 3) a higher rate of engraftment failure, 4) concerns about reduced immunity to infections, 5) reduced anti tumor activity, 6) inability to obtain additional cells from the donor, 7) the difficulty in searching the large number of existing cord blood banks for matched grafts, 8) concerns regarding variations in the required handling and preparation of the units, 9) uncertain expectations for cell recovery after thawing, and 10) concerns regarding the overall quality of UCB among the cord blood banks (2). Hematopoietic stem cell transplantation using umbilical cord blood progenitors in patients is currently being experimented in the clinic. Taken together, there is a clear and urgent need to identify another easily accessible cellular source suitable for hematopoietic transplantation.

The non-hematopoietic component of a normal bone marrow consists of several cell types. Friedenstein (3) was the first investigator who described clonal, fibroblast-like plastic adherent cells from bone marrow capable of differentiating into osteoblasts, adipocytes, and chondrocytes (4-7). These cells, later termed mesenchymal stem cells (MSC), are also stromal cells; the structural components of the bone marrow that support ex vivo culture of hematopoesis by providing extracellular matrix components, cytokines, and growth factors (3,8-12). Numerous investigators have now demonstrated that multipotent MSCs can be recovered from a variety of adult tissues and differentiate into a variety of tissue lineages including myoblasts, hepatocytes, and possibly even neural tissue (13-16). One group has reported that hematopoietic stem cells (HSCs) can be differentiated into multiple blood lineages through the application of a demethylation agent (5aza 2'deoxycytidine) and a deacetylation inhibitor (trichostatin A) (Milhem et al., 2004; US 2005/0276793).

The question of how a single cell can differentiate into the many different cell types has long led to the postulation that additional information that regulates genomic functions must exist beyond the level of the genetic code. This concept led to the introduction of the term "epigenetics" back in the 1940s—a term that has now evolved to mean heritable changes in gene expression that do not involve changes in DNA sequence (32). Epigenetic regulation is not only critical for generating diversity of cell types during mammalian development, but it is also important for maintaining the stability and integrity of the expression profiles of different cell types. Interestingly, whereas these epigenetic changes are heritable and normally stably maintained, they are also potentially reversible, as evidenced by the success of cloning entire organisms by nuclear transfer methods using nuclei of differentiated cells (33).

Studies of the molecular basis of epigenetics have largely focused on mechanisms such as DNA methylation and chromatin modifications (34). In fact, emerging evidence indicates that both mechanisms act in concert to provide stable and heritable silencing in higher eukaryotic genomes. DNA methylation is a biochemical modification that, in human cells, primarily affects cytosines when they are part of the symmetrical dinucleotide CpG. Cytosine methylation has long been a challenging scientific puzzle. In mammals, DNA methylation is essential for normal development, but its evolutionary raison d'être remains controversial. A commonly held hypothesis is that DNA methylation originally evolved to silence repetitive elements, and that this silencing property has also been put to use in other situations where transcriptional silencing is required, such as imprinting (a process whereby one of the two alleles of a gene are permanently inactivated, depending on which parent that allele was inherited from) and X-chromosome inactivation. Most CpG sites have been lost from mammalian genomes during evolution, but about 1% of human DNA consists of short areas where CpG sites have escaped depletion. Most of the remaining CpG sites are normally methylated in adult cells. About half of all genes have a CpG island in their promoter region, and this gene configuration is what has recently attracted the most attention. Most promoter CpG islands are normally unmethylated, regardless of the expression state of the associated gene. However, in silenced areas, such as the inactive X-chromosome in females and the silenced allele of imprinted genes, promoter-associated CpG islands are generally methylated, and this methylation is essential for maintaining the silenced state.

Mechanisms regulating the establishment of methylation remain poorly understood, but the consequences of CpG island methylation are becoming increasingly clear. Methylation triggers the binding of methylated DNA-specific binding proteins to CpG sites, attracting histone-modifying enzymes that, in turn, focally establish a silenced chromatin state. Consistent with a resurgence of interest in the idea that cancer is a disease of faulty development, there has been a revival of interest in the epigenetic processes involved in neoplastic development and progression. The potential reversibility of epigenetic changes through pharmacological manipulation makes this area important in cancer management, and specific DNA methylation inhibitors are currently being used as anti-cancer agents in the USA: 5-Azacytidine has now been approved for use and decitabine proved to be clinically effective in myelodysplastic syndrome and myeloid leukemias (35-37).

Mesenchymal and mesenchymal-like cells (found by the inventors to be applicable to the present invention) have been recovered from a rapidly expanding list of tissues. Exemplary cells can also be recovered from human fat aspirates (38), cryo-preserved human umbilical cord blood (39), placental tissue (40) and (41), and even human exfoliated deciduous teeth (42). Furthermore, a multipotent precursor cell from mammalian dermis that can differentiate into both neural and mesodermal progeny has previously isolated, expanded, and characterized (43, 44), and later this group reported the isolation, expansion, and characterization of a similar precursor cell from neonatal human foreskin tissue. Like their rodent counterparts, the human skin cells grew in suspension as spheres in the presence of the growth factors, fibroblast growth factor 2 and epidermal growth factor and expressed several adhesion molecules and characteristic embryonic transcription factors. These human skin cells could be maintained in culture for long periods of time induce to differentiate into neurons, glia, and smooth muscle cells (45). Most recently, Bartsch et al. isolated MSCs from human postnatal dermal tissues. The isolated cells were expanded and maintained for over 100 population doublings with retention of their chromosomal complement and potential for multilineage differentiation.

Progeny of cell lines established from a single dermal mesenchymal cell could be differentiated into adipogenic, osteogenic, and myogenic lineages, consistent with the conclusion that they established a clonal, multipotential, somatic mesenchymal cell line (46). Because multipotent mesenchymal cells are easily expanded in culture and differentiate into several tissue lineages, there has been much interest in their clinical potential for tissue repair and gene therapy (47). Numerous laboratories have now demonstrated that mesenchymal and mesenchymal-like cells (such as bone marrow derived fibroblastic cells) recovered from a variety of adult tissues differentiate into various tissue lineages in vitro. In particular, Verfaille and colleagues, report that a specific type of murine mesenchymal cells isolated from bone marrow, muscle, or brain, termed multipotential adult progenitor cells (MAPCs), differentiates into a variety of tissue lineages including myoblasts, hepatocytes, and even neural tissue (13-16).

SUMMARY OF THE INVENTION

The present invention is thus directed to the surprising finding that fully differentiated cells, such as human fibroblasts, can be directly transdifferentiated into entirely different cell types, such as hematopoietic cells, through the application of demethylating agents such as agents that inhibit or reverse the methylation status of DNA. The invention is particularly surprising in that it has been discovered that the invention is applicable to a broad range of cells regardless of their differentiation status (as distinct, e.g., from undifferentiated stem cells), and is particularly applicable to starting cells that are not undifferentiated or de-differentiated stem cells, i.e., the invention is surprisingly applicable to the transdifferentiation of CD34-negative cells, that is, cells that do not express cell surface stem cell markers such as CD34.

Accordingly, in certain embodiments, the invention is directed to a method of transdifferentiating cells of a first cell type into cells of a second cell type different from the first cell type, the method comprising culturing the cells of the first cell type in the presence of a demethylating agent in an amount and for a time effective to transdifferentiate said cells to provide a population of cells comprising cells of the second cell type; wherein the first cell type is a CD34-negative cell or a fibroblastic cell. The first cell type may be a fibroblast, such as a skin, foreskin or bone marrow fibroblasts or a fibroblast of a stromal or mesenchymal cell. Notable examples include a bone marrow stromal cell or virtually any cell type of non hematopoietic cells (i.e., a cell that is not a CD34+, CD45+ or a stem cell). Examples include stromal, mesenchymal and fibroblastic cells.

As mentioned, a surprising advantage of the invention is that it permits the direct production of transdifferentiated cells, most notably, hematopoietic cells such as endothelial cells, bone marrow derived fibroblasts, mesenchymal cells, T-cells, monocytic and granulocytic cells as well as B cells. However, most important is the ability to produce second cell types that are, in effect, hematopoietic cells, such as cells that are CD45+. Moreover, second cell populations are generated that include cells that are both CD34+ and CD45+ (i.e., cells that are phenotypically what are referred to as hematopoietic stem cells, or HSCs). Second cell types that are endothelial in nature are also generated by the disclosed methods, cells that may be characterized as, for example, expressing CD133 and/or vascular endothelial growth factor receptor-2 (VEGFR-2). With respect to the generation of hematopoietic cells, it is found that through practice of the invention, cell populations are generated that include a wide variety of hematopoietic cells, including granulocytes and monocytes, B cells and T cells.

In the practice of the invention, it is contemplated that virtually any demethylating agent (i.e., an agent that either promotes demethylation of inhibits methylation) can be employed. However, most preferred will be known demethylating agents such as 5-azacytidine or 5-aza-2-deoxycytidine, zebularine, procaine, epigallocatechin-3-gallate, RG108, 1-β-D-arabinofuranosyl-5-azacytosine, dihydro-5-azacytidine or L-ethionine. Particularly preferred, though, are those that are FDA approved for this purpose, such as 5-azacytidine or 5-aza-2-deoxycytidine.

Practice of the invention is relatively straightforward. The first cell types that one desires to transdifferentiate (or dedifferentiate, as the case may be) are simply cultured in the presence of the demethylating agent for a period of time and at a concentration that will achieve the desired effect. The timing and dosages are not believed to be critical, but it will generally be preferred to expose the selected cell population to the demethylating agent for a period of time of from about 1 minute to about 1 week. However, in preferred embodiments experience has shown that a time period from day 1 and day 3, followed by treatment with growth factors on day 7 and 10. The period between demethylation treatments can also, where desired, be expanded to every 6 days to achieve the desired transdifferentiation.

The amounts of demethylating agent that is employed is, again, not believed to be a critical aspect of the invention and will, of course, depend on the length of time that one desires to culture the cells. Nevertheless, in preferred embodiments, the demethylating agent in included in the culture medium at from about 0.1 µg/ml to about 10 µg/ml, with 2.5 to 5 ug/ml being particularly preferred.

The inventors have determined that substantial advantages, in terms of ease and degree of transdifferentiation, will be realized through the further inclusion of additional growth and conditioning factors. Again, while not absolutely critical, practitioners will find particular advantage through the inclusion of additional growth factors, most notably, growth factors such as granulocyte-macrophage stimulating factor (GM-CSF), stem cell factor (SCF), G-CSF, M-CSF, thrombopoietin, IL-2, IL-4, fibroblast growth factor (FGF), epidermal growth factor (EGF) and/or vascular endothelial growth factor. Of course, it is often the case that more than one growth factor will be included. Preferred combinations include GM-CSF in combination with stem cell factor. The amount of such growth factors that are included will generally be that amount typically used in culture for effecting growth factor action, such as from about 1 ng/ml to about 100 ng/ml, each.

In still further embodiments, the invention is directed to a method of de-differentiating a differentiated cell comprising contacting the cell with a demethylating agent. In such embodiments, the starting cell types will preferably cells such as a CD34-negative cell or a fibroblastic cell, including fibroblasts, such as skin fibroblasts or fibroblasts of a stromal or mesenchymal cell. As before, notable examples include a bone marrow stromal cell or virtually any cell type that is a CD34 negative cell (i.e., a cell that is not a CD34+ or stem cell), including stromal, mesenchymal and fibroblastic cells.

In such embodiments, the method will preferably involve de-differentiation of the starting cell type into a de-differentiated hematopoietic cell, a multipotent cell, a totipotent cell or a stem cell. The method will similarly include the use of conventional demethylating agents such as 5-azacytidine or 5-aza-2-deoxycytidine, zebularine, procaine, epigallocatechin-3-gallate, RG108, 1-β-D-arabinofuranosyl-5-azacytosine, dihydro-5-azacytidine or L-ethionine, with 5-azacytidine or 5-aza-2-deoxycytidine being particularly preferred. Particularly for many medical and therapeutic applications, the foregoing method will further comprise re-differentiating the de-differentiated cell, for example, into an endothelial cell, a granulocyte or a macrophage.

Practice of the invention will provide cell population products that are useful in a wide variety of medical and therapeutic applications. For example, such cells are useful for treating a wide variety of anemic conditions, including those associated with numerous types of cancers. After an ex vivo treatment and expansion of the patient's skin, or stoma-derived fibroblasts with demethylating agents and hematopoietic growth factors, the resulting blood elements can be infused back into the patient. Based on the current invention, the same kind of blood elements generation is also useful for patients undergoing bone marrow transplantation as well as patients with chemotherapy-induced pancytopenia and various conditions of marrow failure and bone marrow fibrosis. As an example, skin or stroma cells can also be generated from any normal donor, transdifferentiated into hematopoietic cells in culture and administered to HLA-matched patients who need them.

Thus, it is contemplated that various therapeutic applications of the transdifferentiated cells of the present invention will involve the administration of cells produced by the disclosed methods to human subjects, such as human cancer patients, or patients suffering from diseases such as bacterial sepsis, septic shock, anemia, granulocytopenia, monocytopenia, lymphopenia, thrombocytopenia, marrow fibrosis, brain stroke, myocardial infarction, coronary artery disease, peripheral vascular disease or a vasculopathy. Still further applications will include administration of the cells to patients suffering from side effects of chemotherapy or viral, fungal, or bacterial infections.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7: Conversion of normal stroma fibroblasts into CD45-positive hematopoeitic cells. The experiment described in FIG. 6 was repeated using MSC from 3 additional normal marrow samples. Results of untreated cells (control), cells treated with growth factors (GM-CSF+SCF), 5-azacytidine (AZA), and 5-azacytidine plus growth factors (AZA+GF) are depicted. In 3 of 4 of these experiments treatment with 5-azacytidine slightly increased the number of cells expressing CD45.

DESCRIPTION OF ILLUSTRATIVE EMBODIMENTS

Figure 1:
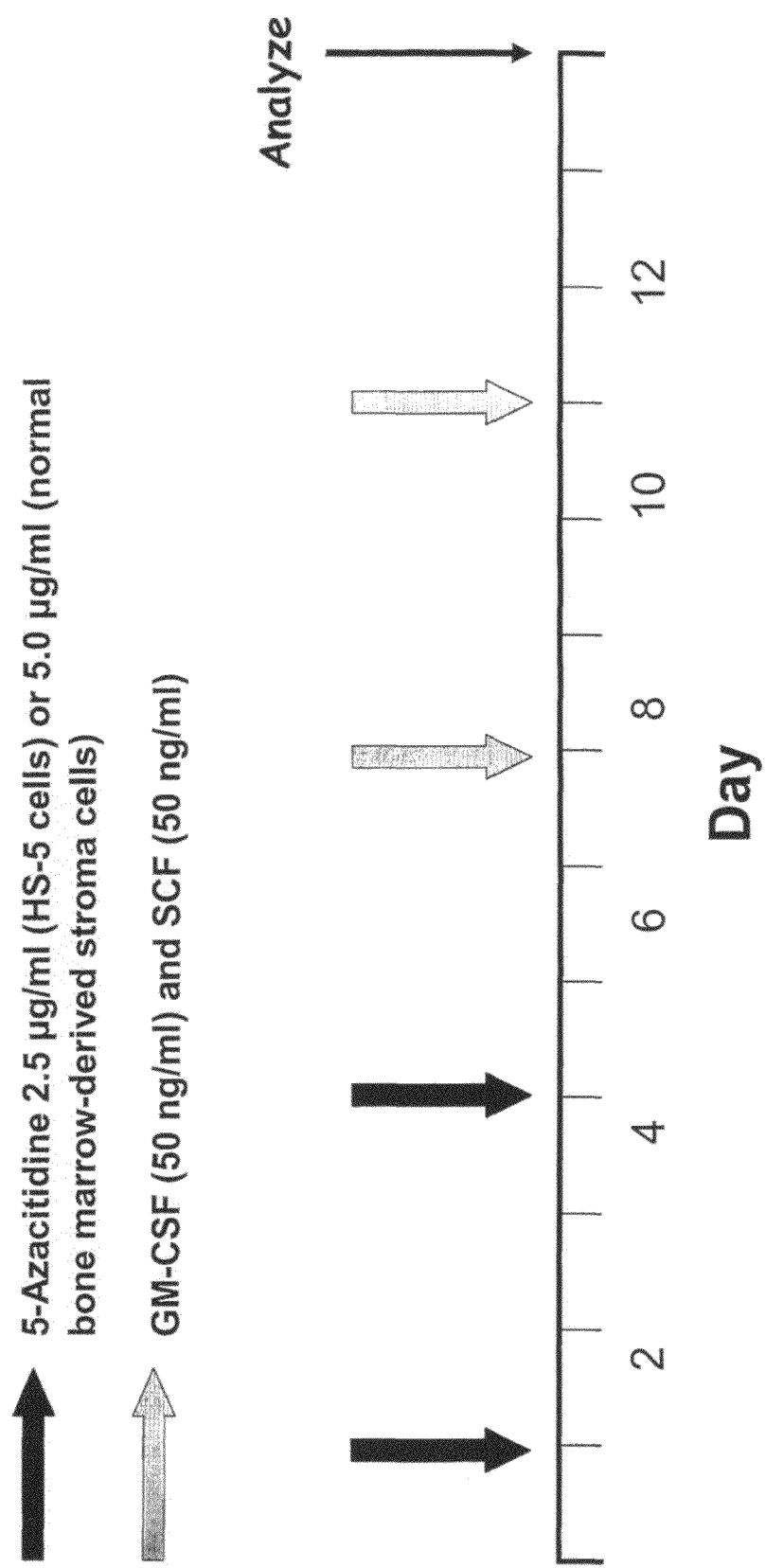
FIG. 1: Conversion of HS-5 fibroblast cell line and normal bone marrow stroma cells into hematopoietic cells by 5-azacytidine and growth factors. In these studies, HS-5 fibroblast cells were transferred to tissue culture flasks as described herein. 2.5 µg 5-azacytidine were added to the culture at days 1 and 4. Granulocyte macrophage colony-stimulating factor (GM-CSF; 50 ng/mL) and stem cell factor (SCF; 50 ng/mL) were added to the culture on days 7 and 10. The cells were harvested and analyzed for the presence of hematopoietic cell surface markets such as CD45 on day 13. Human bone marrow stroma cells were grown from the bone marrow of healthy individuals as described above. When the cultures matured and formed homogenous layers of fibroblast-looking cells (termed mesenchymal stem cells; MSC), the cells were trypsinized and analyzed by fluorescence activated cell scanner/sorter (FACS; above) for the presence of the cell surface marker CD45. When the adherent fibroblast-like MSC became CD45-negative, the cells were harvested and transferred to another tissue flask (day 1 of culture). Five (5.0) µg of 5-azacytidine were added to the culture on days 1 and 4, and GM-CSF and SCF were added to the culture on days 7 and 10 as described above and the cultured cells were analyzed by FACS using the indicated monoclonal antibodies on day 13.

The present invention overcomes limitations in the prior art by providing methods for altering the differentiation state (i.e., "transdifferentiating" or "trans-differentiating") of various cell types by contacting the cell with a demethylating agent. Surprisingly, the inventors have found that a wide variety of cell types, including in vitro expanded cells, can be readily induced to differentiate into hematopoietic cells using a demethylation agent, preferably in combination with one or more growth factors. The inventors envision that these cells can be used in any of a number of clinical applications, such as for hematopoietic stem cell transplantation. The invention is exemplified herein through the transdifferentiation of human foreskin fibroblasts and human bone marrow fibroblasts into a variety of both differentiated and non-differentiated hematopoietic cells, most notably cells that are CD45+. The present invention also provides a method for the generation of endothelial cells from fibroblasts in vitro.

The present invention demonstrates a method of creating blood cells, immune cells and vascular endothelial cells from non-hematopoietic cells. Specifically, non-hematopoietic cells are made to transdifferentiate into several important blood elements including monocytes, granulocytes and lymphocytes. This is achieved by culturing fibroblasts of various sources, including marrow stroma cells, as well as human skin, in the presence of a demethylating agent and hematopoietic growth factors. While the invention is exemplified using skin fibroblasts (e.g., foreskin fibroblasts and fibroblast lines such as HS-5 cells), it is contemplated that hematopoeitic transdifferentiation of cells can be achieved with virtually any type of starting cell, particularly cells that are themselves partially or fully differentiated themselves (such as CD34-negative cells). Thus, while the invention is exemplified using fibroblast cells, it is contemplated that the invention can be readily applied to any partially or fully differentiated starting cells, including cell populations that include less than 25%, and even less than 5%, CD34+ cells. This is an important aspect of the invention in that it permits the use of cell types that are readily available in substantial quantities.

It is important to note, that the invention is useful for treating a wide variety of anemic and bone marrow failure conditions, including those associated with numerous types of cancers. After an ex vivo treatment and expansion of the patient's skin, or stoma-derived fibroblasts with demethylating agents and hematopoietic growth factors, the resulting blood elements can be infused back into the patient. Based on the current invention, the same kind of blood elements generation is also useful for patients undergoing bone marrow transplantation as well as patients with chemotherapy-associated bone marrow failure.

Skin or stroma cells can also be generated from any normal donor, transdifferentiated into hematopoietic cells in culture and administered to HLA-matched patients who need them. The present invention also discloses a method of creating human endothelial cells from fibroblasts. This was achieved by culturing human fibroblasts from various sources in the presence of a demethylating agent with or without epidermal growth factor. This segment of the invention is useful for the generation of endothelial cells from fibroblasts of a patient in vitro and then transplanting them back to the same patient (e.g., in organs that suffered either blockage or reduction of blood supply) in order to allow for the restoration of blood supply.

One type of starting cell that is readily available is substantial quantities are HS-5 cells. A preferred method of transdifferentiating HS-5 cells is relatively straightforward. For example, HS-5 cells can be grown in virtually any appropriate medium, such as alpha MEM (Invitrogen Gibco, Carlsbad Calif.) preferably supplemented with 10% BCS (Hyclone, Logan Utah), and cultured at established conditions, such as at 37° C. with 5% $CO^2$. To expand the cell cultures, the cells can be, for example, subcloned when they reach 80 to 90% confluence. Expansion is then achieved by well known techniques, such as by trypsinized for 10 minutes at 37° C. (trypsin/EDTA, Invitrogen Gibco) and splitting, for example, 1 to 5.

A preferred method for transdifferentiation of cells into hematopoeitic cells employs a combination of the selected demethylating agent together with GMCSF and SCF. In such embodiments, starting cells are cultured for a period of time with the demethylating agent, followed by culturing for a period of time with the inclusion of these growth factors. For example, in the case of HS-5 cells, 5-azacytidine (Vidaza) is added to flasks of HS-5 that are, for example, 60 to 70% confluent, in an amount ranging from 2.5 to 5.0 ug/mL, and the cells are incubated for an appropriate period of time. The inventors have found that a three-day incubation period is fully adequate. However, the incubation time is not believed to be critical. After a period of time, such as three days, the media is replaced, if necessary (e.g., where the media pH has changed), and the 5-azacytidine is added again. After a second period of growth, in this case three days, growth factors (preferably, GMCSF and SCF) are added. The inventors have found that at this point additional media changes should not be necessary. After a third period of incubation, such as a three day incubation, growth factors can added again if necessary. A period of time after the second addition of growth factors, again preferably three days, the cells (both adherent and nonadherent) are harvested and analyzed.

Where endothelial cells are desired instead of hematopoietic cells, the foregoing protocol is employed with the exception that EGF (Biosource, Camarillo, Calif.) is used in place of GMCSF and SCF. In such embodiments, EGF is employed in the secondary cultures in about 7.24%.

In a preferred method for transdifferentiation of other cells, such as normal bone marrow cells, the cells are placed into a flask for a period of time, typically 48 hours is sufficient, in an acceptable growth medium, such as alpha MEM supplemented with 20% BCS. After 48 hours the nonadherent cells are drawn off and placed into a fresh flask and fed with the alpha 20% media. The adherent cells are refed with the alpha 20% media and observed twice weekly for continued growth. The adherent cells are trypsinized and subcloned (1 to 3) when they reach ~80% confluence. After two to three sub-clonings, the cells are screened for CD45 positivity. The cells are subcloned until no CD45 is detected. Then, in order to transdifferentiate the cultured stroma cells into hematopoietic cells, the subcloned stroma cells are incubated in the same way as the HS-5 cells discussed above, except that the inventors prefer to employ a higher concentration of Vidaza (5-azacytidine), typically on the order of 2.5 to 5.0 ug/mL. Where transdifferentiation of stroma cells to endothelial cells are desired, the same approach as employed for HS-5 cells is also employed except, again, the higher concentration of 5-azacytidine is employed.

In still other preferred embodiments, transdifferentiation of other cell types, such as normal human donor fibroblasts is carried out in a similar fashion. In a preferred embodiment, cells are grown in a convenient medium, such as Iscove's media (Invitrogen Gibco) supplemented with 10% BCS (Hyclone) at 37° C. with 5% $CO^2$. The cells are trypsinized and subcloned (1 to 8) when they reach ~80% confluence. If the cells are allowed to reach 100% confluence, they are difficult to trypsinize and will not grow as well after subcloning. For conversion to hematopoietic cells, the cultures, preferably at about ~60% confluence, are treated daily for three days with 5-azacytidine at a concentration of from about 2.5 to 5.0 ug/mL. On the fourth day the cells are treated with both 5-azacytidine and growth factors (GM-CSF and SCF). On the fifth day of culture the cells are treated with growth factors alone. On the sixth day the cells (adherent and nonadherent) are screened. For conversion to endothelial cells, EGF is again substituted for GM-CSF/SCF.

All screening is done using human specific antibodies and their corresponding isotypic controls. Isotypic controls are used on every sample of every experiment to control out nonspecific background fluorescence.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Conversion of a Fibroblast Cell Line and Normal Bone Marrow Stromal Cells into Hematopoietic Cells The present example demonstrates the application of demethylating agents to produce hematopoietic cells from a fibroblast cell line (HS-5) or normal bone marrow stromal cells.
1. Materials and Methods Cell lines. The human bone marrow stroma/MSC cell line HS-5 was obtained from ATCC. These fibroblast-like cells are plastic adherent and grow as a single layer in α-medium (GIBCO, Grand Island, N.Y.) supplemented with 10% fetal calf serum (FCS; Hyclone, Logan, Utah). The cells were gown in tissue culture flasks (Falcon, Bedford, Mass.) at 37° C. in a humidified atmosphere of 5% $CO_2$ in air, their culture media was replaced once a week, and the cells were split at 1:10 and re-plated in identical tissue culture flasks before confluence. In different experiments 5-Azacytidine, granulocyte-macrophage colony-stimulating factor (GM-CSF) and stem cell factor (SCF) were added to the cultures according to the schedule and concentrations depicted in FIG. 1 or FIG. 2. When growth factors were added, α-medium was replaced with Iscove's modified Dulbecco's medium (IMDM; GIBCO).

Human foreskin cells. Fresh human skin fibroblasts were purchased from Cambrex (Walkersville, Md.). The cells were grown in tissue culture flasks (Falcon) in fibroblast growth media (Cambrex; supplemented with 2% FCS, recombinant human fibroblast growth factor and bovine insulin) at 37° C. in a humidified atmosphere of 5% $CO_2$ in air. The cells grew in monolayers. Their culture media were replaced weekly and they were split before confluence at 1:7 into identical tissue culture flasks. In different experiments 5-Azacytidine, granulocyte-macrophage colony-stimulating factor (GM-CSF) and stem cell factor (SCF) were added to the cultures according to the schedule and concentrations depicted in FIG. 2. When growth factors were added to culture, the fibroblast growth media was replaced with IMDM (GIBCO) supplemented with 2% FCS.

Bone marrow cells. Bone marrow aspirates were obtained from hematologically healthy donors after obtaining the donors' informed consent following the approval of the Institutional Review Board at The University of Texas M. D. Anderson Cancer Center. The bone marrow cells were left over cells from bone marrow aspirates performed as part of a medical workup.

Generation of Bone Marrow Stroma Cell Cultures. Low-density bone marrow cells were obtained by Ficoll Hypaque fractionation and cultured in tissue culture flasks (Falcon) in α-medium (GIBCO) supplemented with 20% FCS (Hyclone) at 37° C. in a humidified atmosphere of 5% $CO_2$ in air. The culture medium and floating cells were completely aspirated and replaced with fresh tissue culture medium. Upon confluence, cells were exposed to 0.05% trypsin and 0.53 mM EDTA (GIBCO) at 37° C. for 10 min. Following incubation, FCS (v/v) was added for 5 min., the cells were removed from the tissue culture flasks, washed in PBS, transferred to new tissue culture flasks at a low density, and incubated with fresh tissue culture media. The cells were expanded and tested until all hematopoietic elements were no more present and all cells were CD45-negative.

Flow cytometry. To determine whether 5-Azacytidine treatment induced demethylation, we used an antibody that detects the presence of 5-methylcytidine as a marker of global DNA methylation by flow cytometry, as previously described (48, 50). Briefly, cells were permeated using the Cytofix-Cytoperm kit (Becton Dickinson, San Diego, Calif.) in accordance with the manufacturer's instructions. Briefly, cells were were fixed with cytofix buffer containing PBS and paraffin aldehyde, washed in PBS and exposed for 5 min to Cytoperm solution containing saponin. The cells were washed again in PBS and incubated for 30 min at 37° C. with anti-5-methylcytidine antibodies (CalBiochem, San Diego, Calif.), washed in PBS and analyzed by flow cytometry. To detect the presence of the cell surface CD45 antigen, cells were incubated for 30 min. at 37° C. with anti-CD45 antibodies (Becton Dickinson), washed in PBS and analyzed by flow cytometry. Flow cytometric analysis was performed using a FACSCalibur flow cytometer and the CellQuest software program (Becton Dickinson Immunocytometry Systems, San Jose, Calif.). Data analysis was performed using CellQuest and the Modfit LT V2.0 software program (Verity Software House, Topsham, Me.).

Colony-forming unit granulocyte-macrophage (CFU-GM) colony culture assay. The colony-forming unit-granulocyte-macrophage (CFU-GM) clonogenic assay was performed as previously described (49). Briefly, $2 \times 10^5$ treated and untreated cells were cultured in 0.8% methylcellulose in IMDM (GIBCO) supplemented with 10% FCS, and 50 ng/ml recombinant human granulocyte-macrophage colony-stimulating factor. Next, 1.0 ml of the culture mixture was placed in 35-mm Petri dishes in duplicate and incubated at 37° C. in a humidified atmosphere of 5% $CO_2$ in air. All cultures were evaluated after 14 days for the number of CFU-GM colonies, defined as a cluster of more than 50 cells containing granulocytes, monocytes and macrophages. To identify the cells comprising the CFU-GM colonies, single colonies were microaspirated at random, transferred to glass slides, dried and stained with Write's stain and microscopically analyzed.

2. Conversion of HS-5 and Normal Marrow Stroma Cells to CD45+ Cells

FIG. 1 depicts the culturing and timing of addition of demethylating agent (2-azacytidine) and growth factors (GM-CSF and SCF) to transdifferentiate HS-5 and normal marrow stroma cells into hematopoietic cells.

For the HS-5 cultures, HS-5 fibroblast cells were transferred to tissue culture flasks as described. 2.5 µg, or 5 ug/ml of 5-azacytidine were added to the culture at days 1 and 4. Granulocyte macrophage colony-stimulating factor (GM-CSF; 50 ng/ml) and stem cell factor (SCF; 50 ng/ml) were added to the culture on days 7 and 10. The cells were harvested and analyzed for the presence of hematopoietic cell surface markets such as CD45 on day 13.

Figure 14:
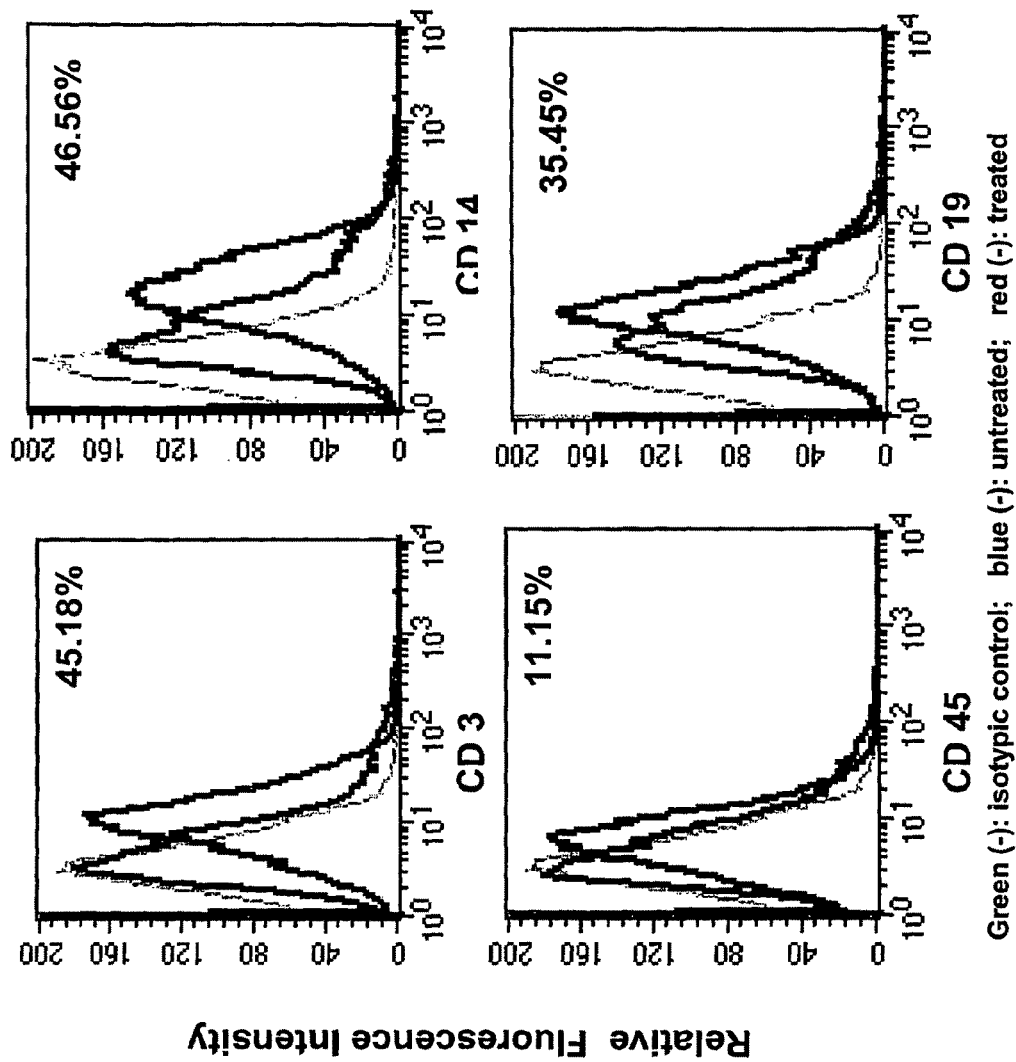
FIG. 14: Converted human foreskin fibroblasts co-express CD34 and CD45. Human skin fibroblasts were incubated with 5-azacytidine (AZA) and growth factors (50 ng/mL GM-CSF and 50 ng/mL SCF). AZA was added to the cultures on days 1, 2, 3, and 4, whereas growth factors were added on days 4 and 5. The cultures were analyzed on day 6. Treated and untreated cells were stained with anti-CD34 PE and anti-CD45 FITC and analyzed by FACS as described above. As shown in the upper corner of the right panel, 2.37% of the AZA and growth factor-treated cells were CD34$^+$CD45$^+$.

FACS analysis of the cell products generated by the foregoing treatment using monoclonal antibodies for CD45, CD3, CD14 and CD19 (FIG. 14) demonstrated that approximately 45% of the cells were CD3 positive, about 46% were CD 14 positive, about 11% were CD45 positive and about 35% were CD 19 positive. This demonstrates the differentiation of skin fibroblasts into hematopoietic cells of the myeloid and lymphoid lineage (both T and B cells). Furthermore, the fact that a fraction of the cells co-express CD45 and CD34, and that these cells have the capacity to engraft NOD/SCID mice and can be transplanted into a second generation of mice, indicates the conversion of skin fibroblasts into hematopoietic stem cells with self renewal capacity.

For the normal marrow stoma cultures, human bone marrow stroma cells were grown from the bone marrow of healthy individuals as described above. When the cultures had matured and formed homogenous layers of fibroblast-looking cells, the cells were trypsinized and analyzed by fluorescence activated cell scanner/sorter (FACS; above) for the presence of the cell surface marker CD45. When the adherent fibroblast-like cells became CD45-negative, the cells were harvested and transferred to another tissue flask (day 1 of culture). Five (5.0) µg of 5-azacytidine were added to the culture on days 1 and 4, and GM-CSF and SCF were added to the culture on days 7 and 10 as described above and the cultured cells were analyzed by FACS using the indicated monoclonal antibodies on day 13.

3. Conversion of Normal Human Fibroblasts into CD45 Positive Cells

Figure 2:
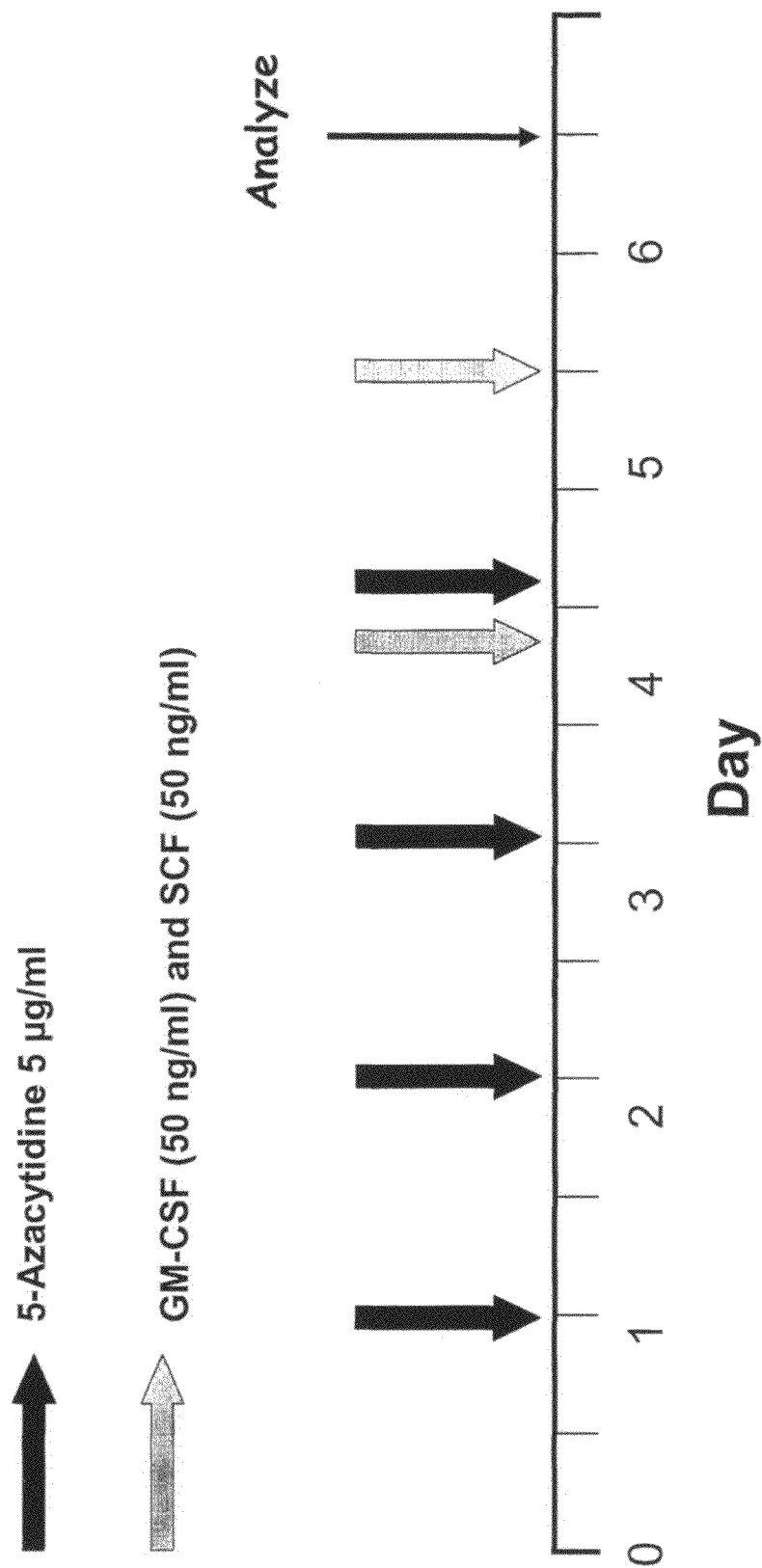
FIG. 2: Conversion of normal human fibroblasts into CD45-positive cells by 5-azacytidine and growth factors. Human fibroblasts were grown in culture as described above. Five µg of 5-azacytidine were added to the cultures on days 1, 2, 3, and 4, and GM-CSF and SCF at the above mentioned concentrations were added on days 4 and 5. The cells were harvested and analyzed by FACS using the indicated monoclonal antibodies on day 6.

FIG. 2 shows the conversion of normal human fibroblasts into CD45-positive cells. In these studies, human fibroblasts were grown in culture as described above. Five µg of 5-azacytidine were added to the cultures on days 1, 2, 3, and 4, and GM-CSF and SCF at the above mentioned concentrations were added on days 4 and 5. The cells were harvested and analyzed by FACS using the indicated monoclonal antibodies on day 6.

4. 5-Azacytidine Reduces the Level of Methylated DNA in HS-5 Cells

Figure 3:
FIG. 3: Azacytidine hypomethylates HS-5 cells. This experiment shows that 5-azacytidine hypomethylates HS-5 cells. HS-5 cells were treated w/ and w/o 5-azacytidine 2.5 uM overnight. After incubation the cells were harvested and washed in PBS. The cells were then fixed and permeabilized using the BD Cytofix/Cytoperm kit (BD Biosciences, San Diego Calif.) as per the kit instructions. After fixation and permeabilization the cells were stained using mouse anti 5-methylcytadine (Serotec Inc., Raleigh N.C.) for 30 minutes. After washing the cells 3 times in the Permwash buffer provided with the BD kit, the mouse antibody was then detected using an RPE labeled rabbit anti mouse IgG (Serotec) for 30 minutes. After 3 additional wash steps, the cells were resuspended in staining buffer (as per the BD kit) and analyzed on a FACSCaliber flow cytometer (BD Immunnocytometry Systems, La Jolla Calif.) for any decrease in 5-methylcytidine. Isotypic antibody was also substituted for anti 5-methylcytidine antibody in treated and untreated cells to control out any background staining.
Figure 3:
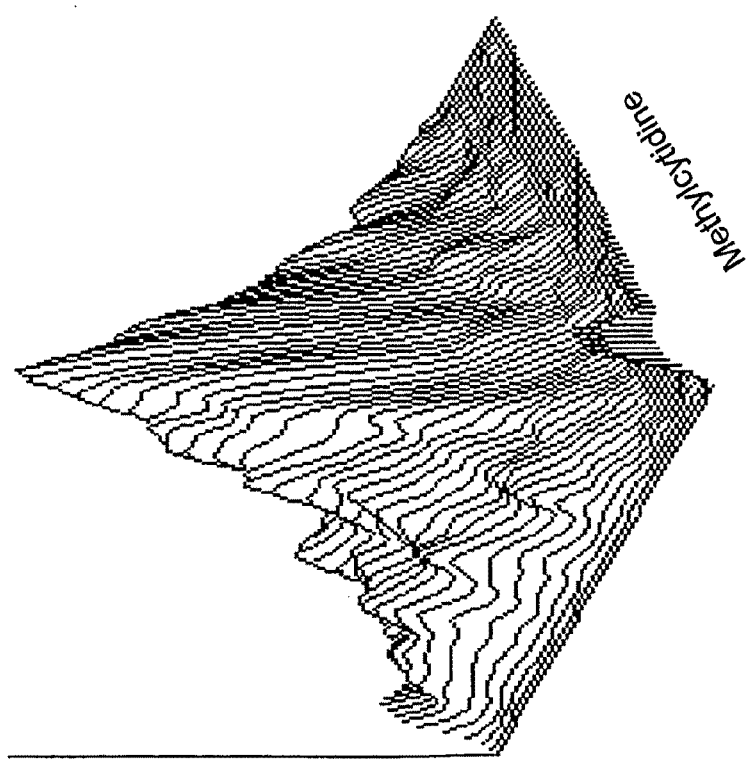

FIG. 3 shows that 5-azacytidine hypomethylates HS-5 cells. HS-5 cells were treated w/ and w/o 5-azacytidine 2.5 uM overnight. After incubation the cells were harvested and washed in PBS. The cells were then fixed and permeabilized using the BD Cytofix/Cytoperm kit (BD Biosciences, San Diego Calif.) as per the kit instructions. After fixation and permeabilization the cells were stained using mouse anti 5-methylcytadine (Serotec Inc., Raleigh N.C.) for 30 minutes. After washing the cells 3 times in the Permwash buffer provided with the BD kit, the mouse antibody was then detected using an RPE labeled rabbit anti mouse IgG (Serotec) for 30 minutes. After 3 additional wash steps, the cells were resuspended in staining buffer (as per the BD kit) and analyzed on a FACSCaliber flow cytometer (BD Immunnocytometry Systems, La Jolla Calif.) for any decrease in 5-methylcytidine. Isostypic antibody was also substituted for anti 5-methylcytidine antibody in treated and untreated cells to control out any background staining.

Example 2

Figure 4:
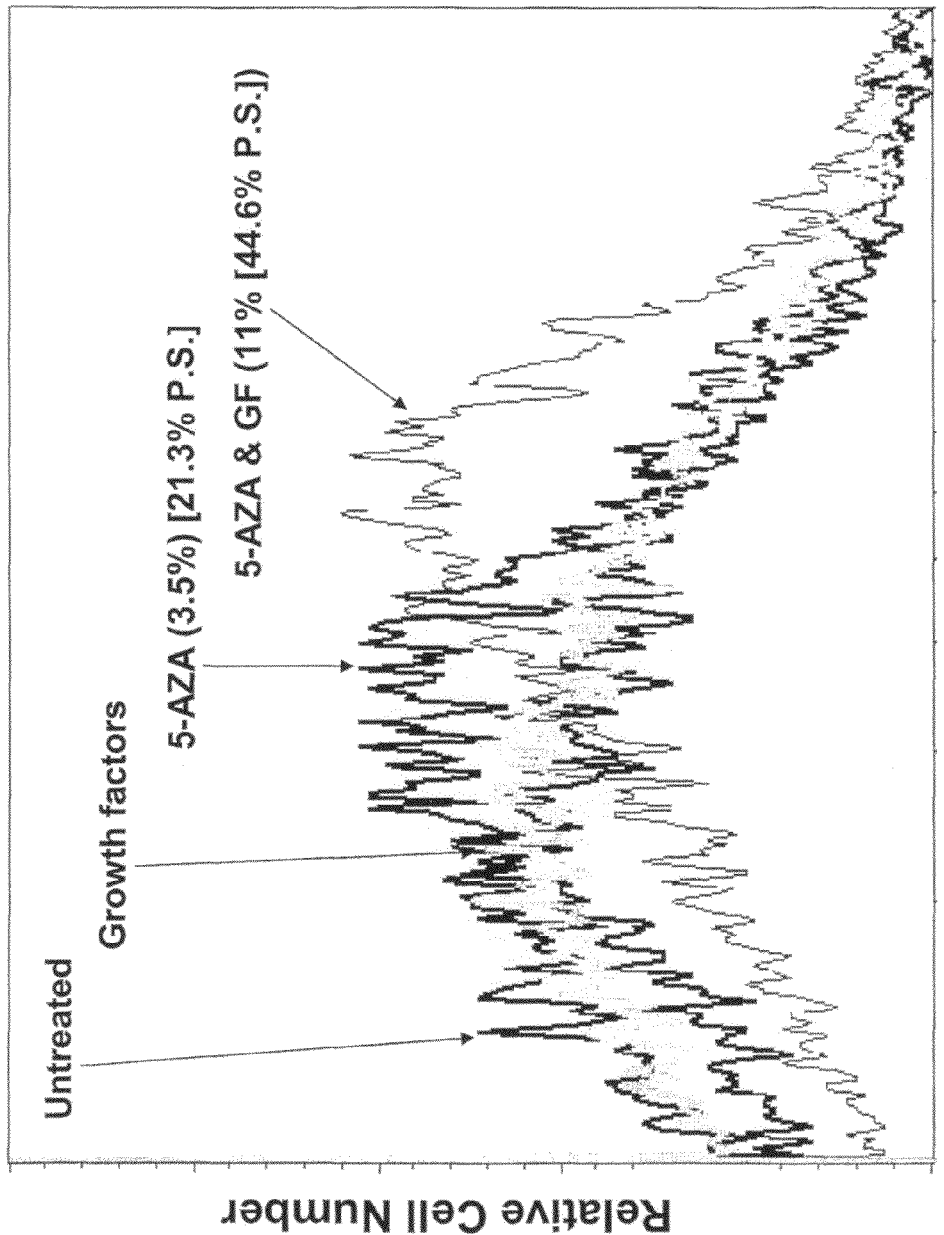
FIG. 4: CD45 expression in 5-azacytidine—and/or growth factor (GM-CSF and SCF)-treated HS-5 cells. HS-5 cells were incubated with or without 5-azacytidine and/or growth factors according to the schedule described in FIG. 1. On day 13 the cells were harvested and analyzed for the presence of cell surface CD45 by FACS. All viable cells were analyzed and the CD45-corresponding isotypic control was used. Untreated cells and cells treated with GM-CSF and SCF alone did not express CD45. In contrast, 3.5% of the cells treated with 5-azacytidine and 11% of the cells treated with 5-azacytidine expressed CD45.

Transdifferentiation of Cells Into Hematopoietic Cells Using 5-Azacytidine and Other Growth Factors FIG. 4 demonstrates that when the CD45 negative HS-5 human fibroblast cell line was treated with the drug 5-azacytidine in the presence of the growth factors GM-CSF and stem cell factor, about 11% of the cells express the hematopoietic marker CD45. The expression of CD45 is time dependent, beginning at day three after the setting of the culture. In these studies, HS-5 cells were incubated with or without 5-azacytidine and/or growth factors according to the schedule described in FIG. 1. On day 13 the cells were harvested and analyzed for the presence of cell surface CD45 by FACS. All viable cells were analyzed and the CD45-corresponding isotypic control was used. Untreated cells and cells treated with GM-CSF and SCF alone did not express CD45. In contrast, 3.5% of the cells treated with 5-azacytidine and 11% of the cells treated with 5-azacytidine expressed CD45.

Figure 5:
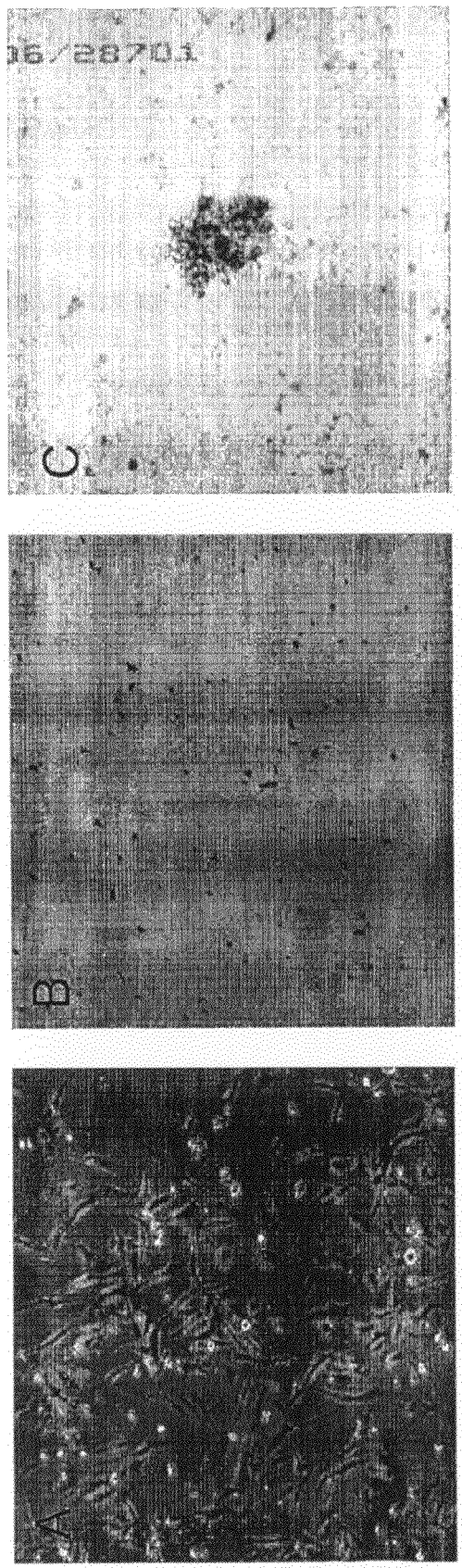
FIG. 5: HS-5 cells transdifferentiate into hematopoietic colony-forming cells. Converted (see FIG. 1) and untreated HS-5 cells were harvested from the tissue culture flasks and culture in methylcellulose in a cl0nigtenic assay in the presence of 50 ng/mL GM-CSF, 50 ng/mL SCF and erythropoietin as described above. After 14 days the cultures were examined using an inverted microscope. The figure shows HS-5 cells grown in culture (A), untreated HS-5 cells grown in methylcellulose (B), and a hematopoeitic (CFU-GM) colony formed from converted (5-azacytidine—and growth factor-treated) cells (C).

Converted (see FIG. 1) and untreated HS-5 cells were harvested from the tissue culture flasks and culture in methylcellulose in a cl0nigtenic assay in the presence of 50 ng/mL GM-CSF, 50 ng/mL SCF and erythropoietin as described above. After 14 days the cultures were examined using an inverted microscope. The figure shows HS-5 cells grown in culture (FIG. 5A), untreated HS-5 cells grown in methylcellulose (FIG. 5B), and a hematopoeitic (CFU-GM) colony formed from converted (5-azacytidine—and growth factor-treated) cells (FIG. 5C). Microscopic evaluation of the colonies obtained following 5-Azacytidine treatment revealed characteristics of mixed granulocyte macrophage lineage (FIG. 5C) as distinguished from untreated cells grown in liquid culture (FIG. 5A) or plated on methylcellulose (FIG. 5B).

Example 3

Figure 6:
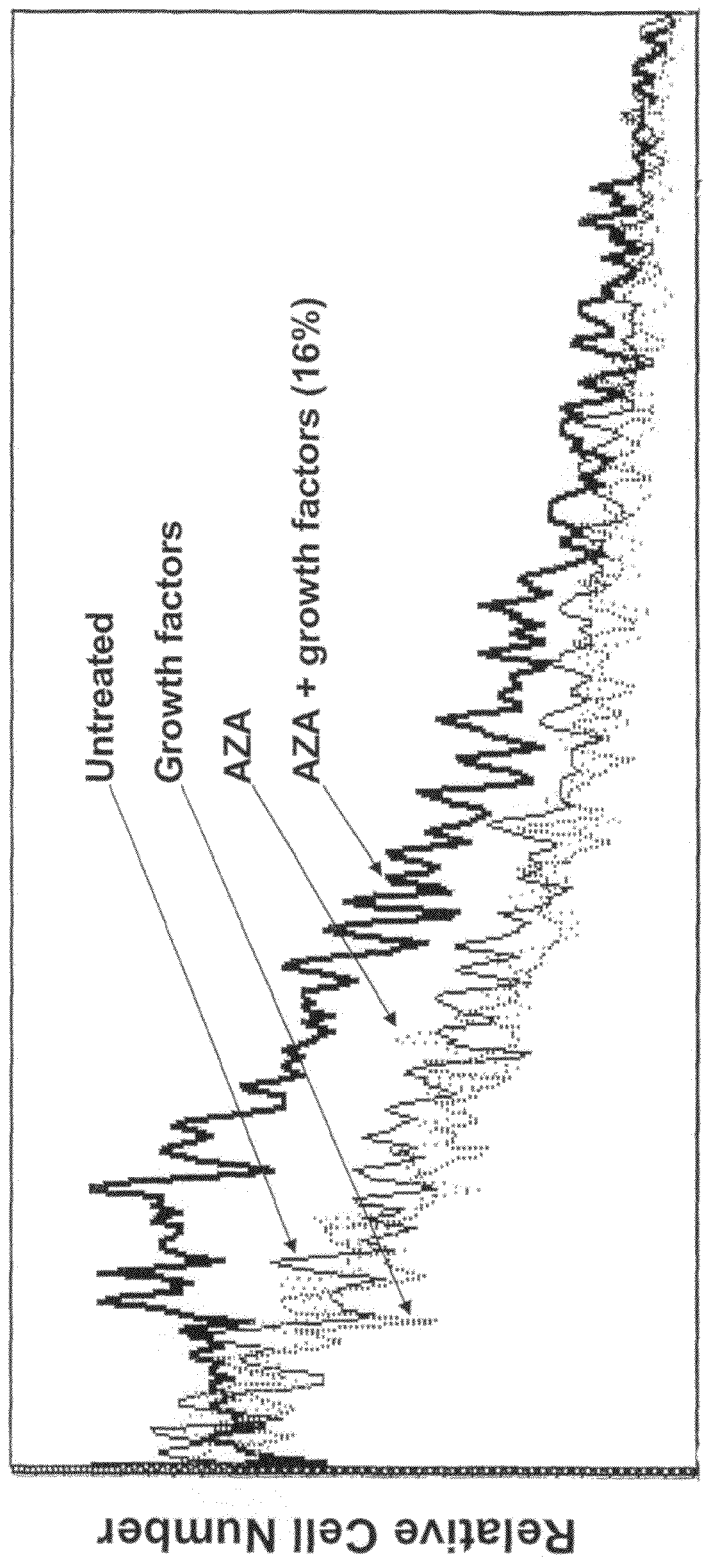
FIG. 6: CD45 expression in 5-azacytidine—and/or growth factor (GM-CSF and SCF)-treated normal bone marrow stroma (MSC) CD45-negative cells. Normal bone marrow adherent cells were grown in culture until they formed a monolayer of CD45-negative cells (tested as described above). Untreated, 5-azacytidine—and/or growth factor (GM-CSF plus SCF)-treated cells (in accordance with the protocol presented in FIG. 1) were evaluated on day 13 of culture for the presence of the cell surface marker CD45 by FACS analysis. A CD45-corresponding isotypic control antibody was used. As demonstrated in this figure, 16% of the CD45-negative normal marrow MSC converted into CD45-poisitve cells after treatment with 5-azacytidine and growth factors (GM-CSF+SCF). Untreated cells, cells treated with only 5-azcytidine or growth factors remained CD45-negative.

Transdifferentiation of Bone Marrow-Derived Human Stroma Cells into Hematopoietic Cells In the next experiment, the effect of DNA demethylation was tested in normal human bone marrow stromal cells. Normal bone marrow adherent cells were grown in culture until they formed a monolayer of CD45-negative cells (tested as described above). Untreated, 5-azacytidine—and/or growth factor (GM-CSF plus SCF)-treated cells (in accordance with the protocol presented in FIG. 1) were evaluated on day 13 of culture for the presence of the cell surface marker CD45 by FACS analysis. A CD45-corresponding isotypic control antibody was used. As demonstrated in this figure, 16% of the CD45-negative normal marrow mesenchymal cells (i.e., bone marrow derived fibroblastic cells) converted into CD45-positive cells after treatment with 5-azacytidine and growth factors (GM-CSF+SCF). Untreated cells, cells treated with only 5-azcytidine or growth factors remained CD45-negative. FIG. 6 shows that up to 16% of bone marrow-derived human stroma cells treated with both 5-Azacytidine and growth factors became hematopoietic cells, as determined by CD45 expression. Treatment with growth factors alone, or with 5-Azacytidine alone, was unable to give rise to a significant number of blood cells.

This experiment was reproduced in three additional human donors of bone marrow stromal cells (FIG. 7). In every donor, the treatment of stroma cells with 5 azacytidine and growth factors resulted in a significant increase of hematopoietic cells. This data extends the previous observation performed with the human fibroblast cell line.

Figure 13:
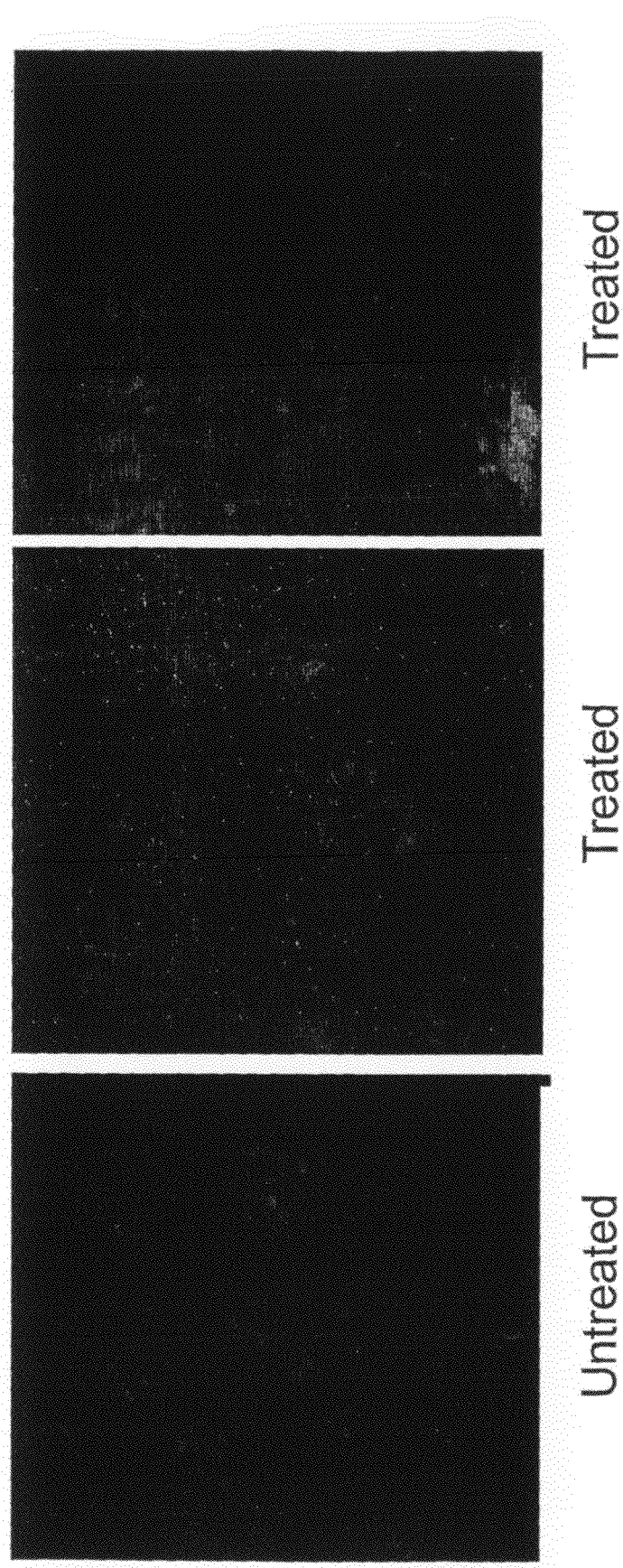
FIG. 13: Transdifferentiation of HS-5 cells generates CD3, CD14 and CD19 positive cells. HS-5 cells were incubated with or without 5-azacytidine and/or growth factors according to the schedule described in FIG. 1. On day 13 the cells were harvested and analyzed for the presence of the indicated human cell surface markers FACS. As shown before the results demonstrate a dramatic increase in CD45+ cells. The figure also shows that in addition to the generation of hematopoietic cells, treatment of HS-5 cells with 5-azacytidine and growth factors give rise to T cells (CD3), B cells and pre B cells (CD19) and to cells expressing the CD14 antigen (macrophages, monocytes, granulocytes and dendritic cells).

Then, to determine into which hematopoietic lineage HS-5 cell trasdifferentiate, cells were harvested on day 13 and analyzed for the presence of various human cell surface markers by FACS (FIG. 13). As shown before, the results demonstrate a dramatic increase in CD45+ cells. FIG. 13 also shows that in addition to the generation of hematopoietic cells, treatment of HS-5 cells with 5-azacytidine and growth factors give rise to T cells (CD3), B cells and pre B cells (CD19) and to cells expressing the CD14 antigen (macrophages, monocytes, granulocytes and dendritic cells).

Example 4

Transdifferentiation of Fibroblasts into Hematopoietic Cells

Figure 8:
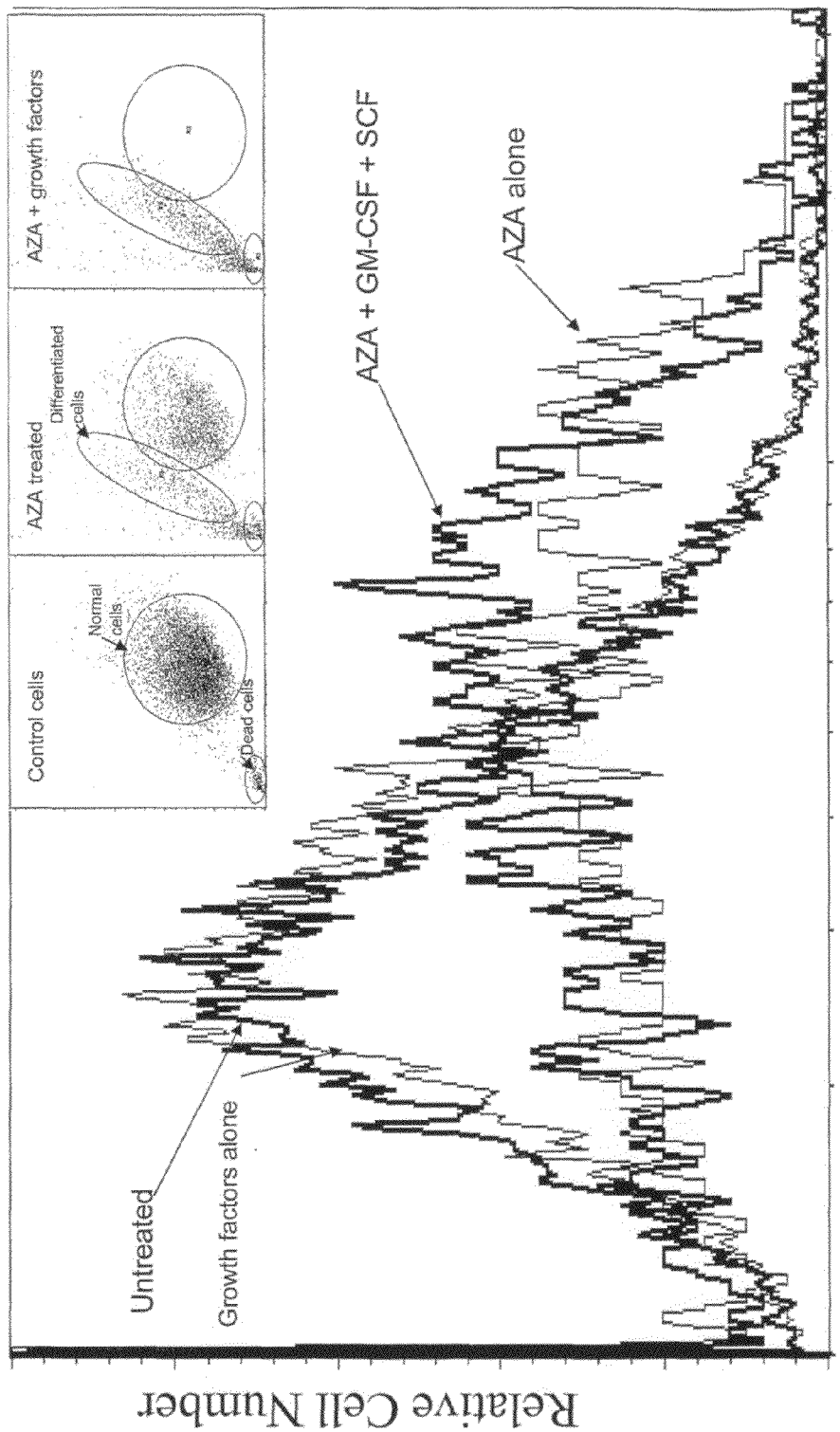
FIG. 8: Conversion of normal human foreskin fibroblasts to CD45-poisitve cells by 5-azacytidine and growth factors. Normal human foreskin fibroblasts were treated with 5-azacytidine and/or growth factors as described in FIG. 2. Treatment of the cells with 5-azacytidine (AZA) and AZA+growth factors (GM-CSF+SCF) converted them into CD45-positive cells as assessed by the above described FACS analysis. The insert shows lateral scatter (Y axis) and forward scatter (X axis) analysis of the entire cellular population of cells. The left insert panel shows the distribution of the entire population of fibroblasts (normal cells aqnd a few dead cells). Treatment with AZA (middle panel) generates a new transdifferentiated ("differentiated") population of cells and the treatment of AZA+growth factors (right panel) abolishes the "normal cell" population.

In order to exclude the possibility that only fibroblasts from a specialized tissue, such as those derived from the bone marrow compartment, are capable of being converted to blood elements, the inventors used normal human foreskin fibroblasts as a model system. In these studies, normal human foreskin fibroblasts were treated with 5-azacytidine and/or growth factors as described in FIG. 2. As shown in FIG. 8, treatment of the cells with 5-azacytidine (AZA) and AZA+ growth factors (GM-CSF+SCF) converted them into CD45-positive cells as assessed by the above described FACS analysis. The insert shows lateral scatter (Y axis) and forward scatter (X axis) analysis of the entire cellular population of cells. The left insert panel shows the distribution of the entire population of fibroblasts (normal cells and a few dead cells). Treatment with AZA (middle panel) generates a new transdifferentiated ("differentiated") population of cells and the treatment of AZA+growth factors (right panel) abolishes the "normal cell" population. Thus, once again, the treatment of those cells with 5-azacytidine and growth factors resulted in similar results to what is described above (about 13% CD45 positive cells). Specifically, the treatment gave rise to a significant portion of the cells expressing the hematopoietic marker CD45. These experiments demonstrate that human skin fibroblasts have the capability and the capacity to be converted into blood elements.

Example 5

Repopulation of the Immune System in Immunodeficient Mice In Vivo

Materials and Methods: SCID mice were lightly irradiated at 30 Gy and administered I.V. with $1 \times 10^7$ cells of the human stroma fibroblast line (HS-5) that were treated with the combination of 5-Azacytidine plus GM-CSF and SCF as described above. The control group received the same number of cells cultured in medium only.

At the indicated times, the mice were sacrificed and a bone marrow cells were harvested and either stained immediately for FACS analysis, or were placed on a glass slide for immunohistochemistry analysis. For both FACS and immunohistochemistry analysis, the primary antibody was mouse anti human HLA-ABC (Obtained from B.D. Biosciences Pharmingen, San Diego, Calif.). Before the cells were injected in vivo, the inventors analyzed the reprogramming of human stroma (HS-5) cells treated with the drug plus the hematopoietic growth factors and control (medium) treated cells for the presence of CD45 cells. It was found that that 7% of the reprogrammed cell preparation and less than 1% of medium-treated cell preparation were CD45 positive.

Figure 10:
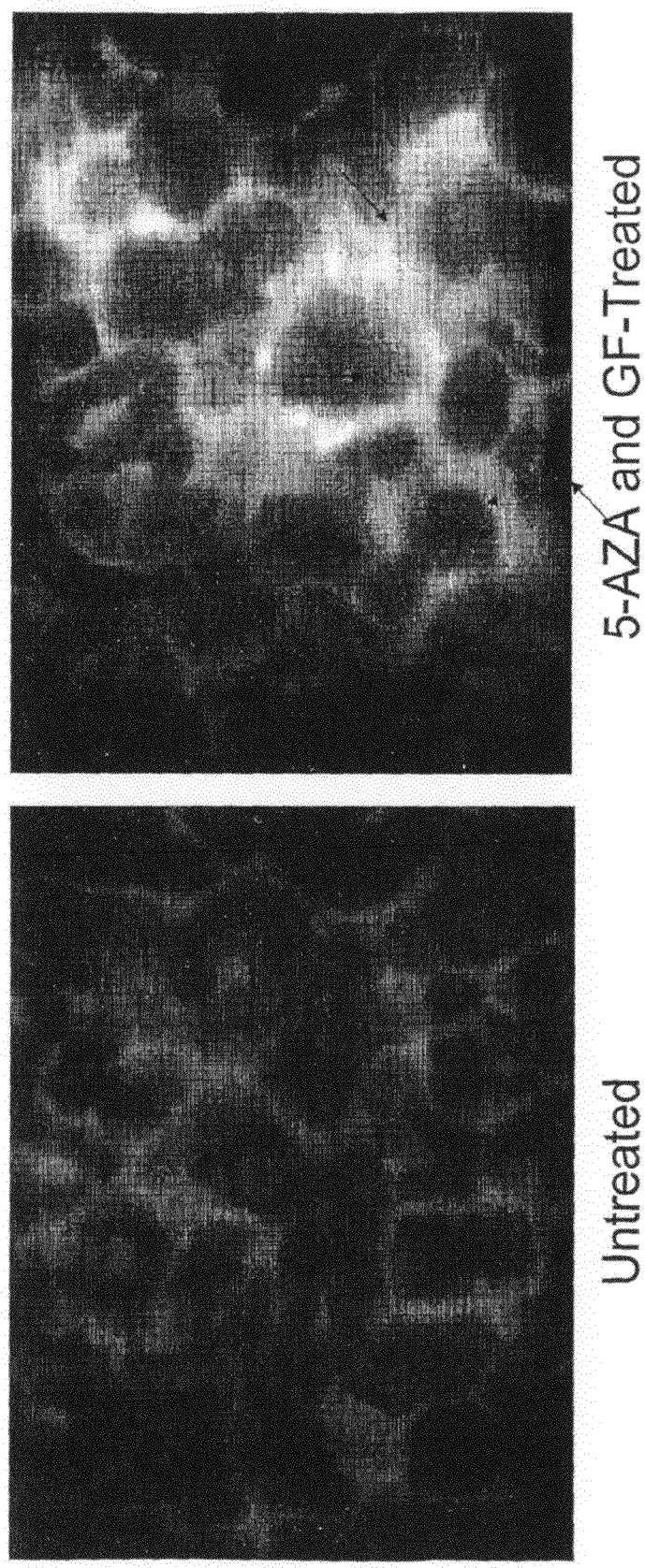
FIG. 10: Immunohistochemical detection of HLA-ABC in NOD/SCID mouse bone marrow cells 3 weeks after injection of 5-azacytidine and growth factor-treated HS-5 cells. HS-5 cells treated with 5-azacytidine and growth factors (GM-CSF and SCF, according to the schedule presented in FIG. 1) and untreated HS-5 cells were injected into the tail vein of NOD/SCID mice 3 hours after exposure to sub-lethal radiation (30 Gy). Bone marrow cells were harvested 3 weeks after injection, cytocentrifuged and immunohistochemically stained with anti-HLA-ABC antibodies. The left panel shows bone marrow cells harvested from and mouse injected with untreated HS-5 cells. The right panel shows bone marrow cells harvested from a mouse that was injected with AZA+ growth factor-treated cells. The HLA-ABC-positive cells are round with big nuclei morphologically different from mouse bone marrow cells.

The inventors addressed the issue of the ability of reprogrammed cells to be transplanted in vivo. HS-5 cells treated with 5-azacytidine and growth factors (GM-CSF and SCF, according to the schedule presented in FIG. 1) and untreated HS-5 cells were injected into the tail vein of NOD/SCID mice 3 hours after exposure to sub-lethal radiation (30 Gy). Bone marrow cells were harvested 3 weeks after injection, cytocentrifuged and immunohistochemically stained with anti-HLA-ABC antibodies. FIG. 10 shows that bone marrow aspirate from mice receiving transdifferentiated cells, but not those receiving control cells were positive for HLA staining as analyzed by immunohistochemistry. The arrow in the slide shows HLA positive cells. The marrow was taken at 3 weeks post I.V. injection. The left panel shows bone marrow cells harvested from a mouse injected with untreated HS-5 cells. The right panel shows bone marrow cells harvested from a mouse that was injected with AZA+growth factor-treated cells. The HLA-ABC-positive cells are round with big nuclei and were morphologically different from mouse bone marrow cells.

Figure 11:
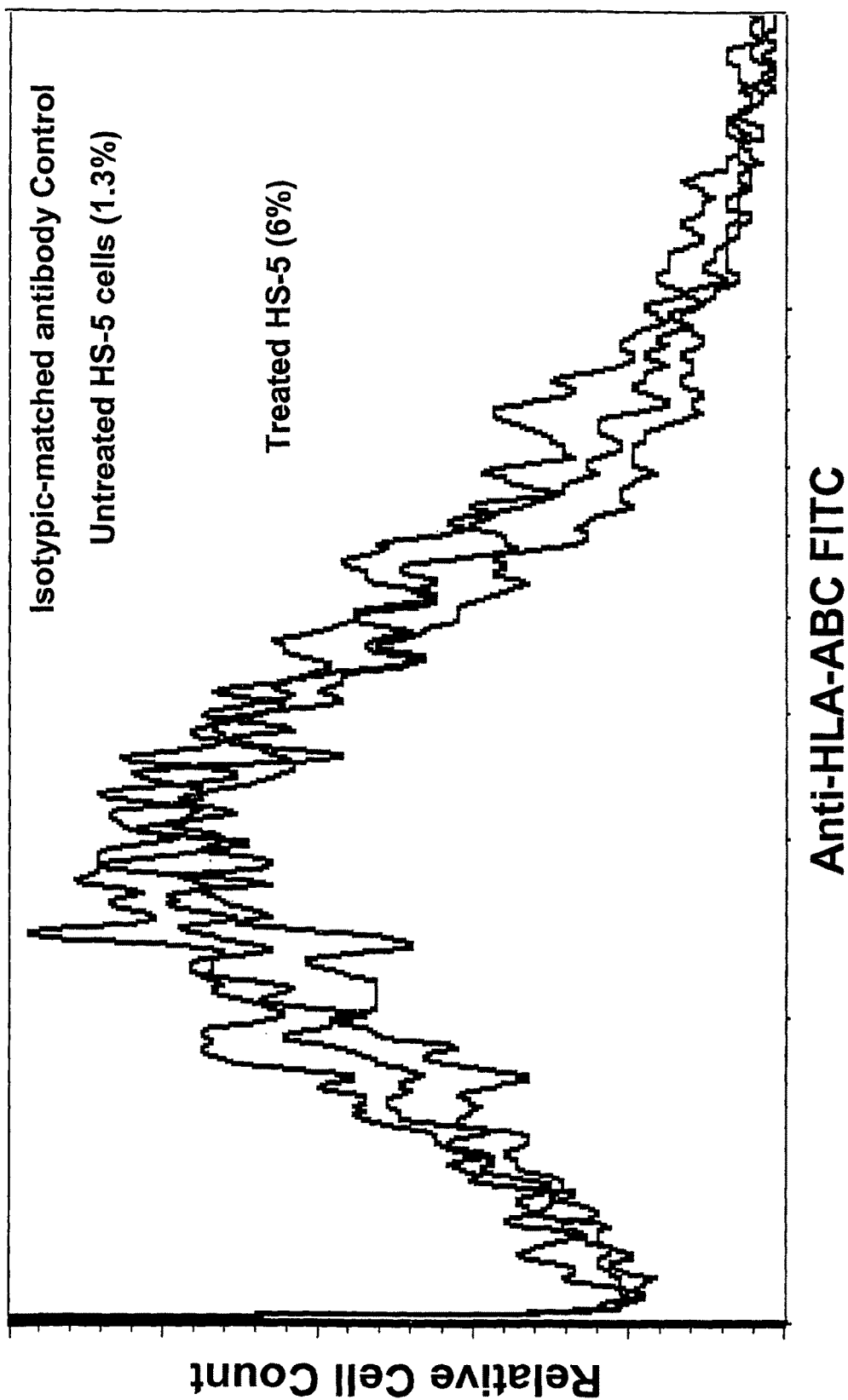
FIG. 11: FACS analysis of mouse bone marrow cells 6 weeks following injection of HS-5-treated or untreated cells. Mouse bone marrow cells from the experiment presented in FIG. 10 were harvested 6 weeks after injection and examined for the presence of cells expressing HLA-ABC by FACS analysis. Bone marrow cells from animals injected with untreated HS-5 cells did not express HLA-ABC whereas 6% of bone marrow cells obtained from mice that were injected with treated HS-5 cells were HLA-ABC-positive.

These results were further validated in the next experiment. Mouse bone marrow cells, instead of being analyzed after 3 weeks (as in the experiment presented in FIG. 10) were harvested 6 weeks after injection and examined for the presence of cells expressing HLA-ABC by FACS analysis. Bone marrow cells from animals injected with untreated HS-5 cells did not express HLA-ABC (1.3% expression, similar to the isotypic control) whereas 6% of bone marrow cells obtained from mice that were injected with treated HS-5 cells were HLA-ABC-positive. As shown in FIG. 11, mice receiving control cells showed less than 1% of HLA staining, whereas about 6% of all marrow cells from mice receiving transdifferentiated cells were HLA-ABC positive.

Figure 12:
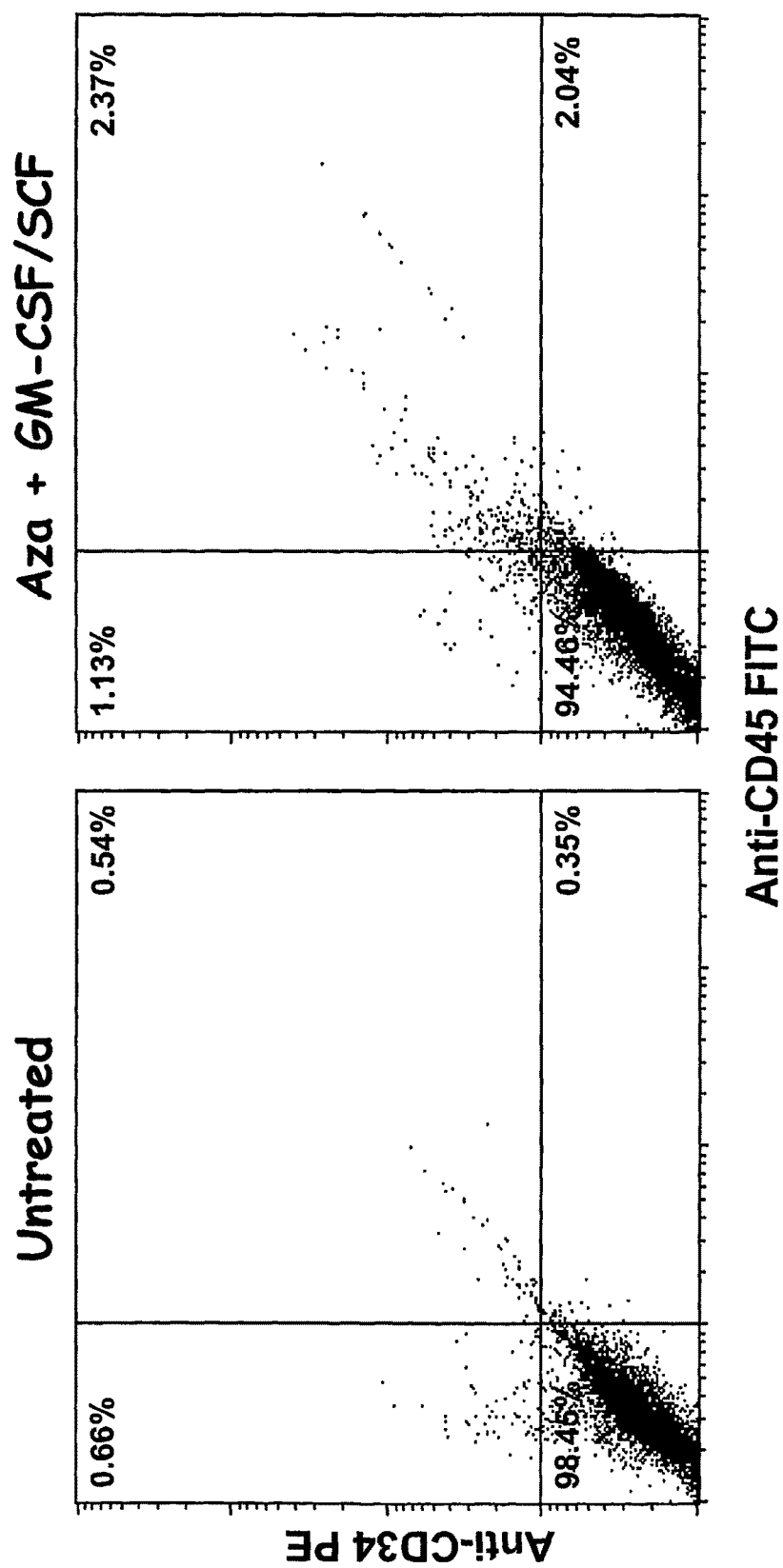
FIG. 12: Second generation transplantation of marrow cells from mice engrafted with transdifferentiated HS-5 cells. HS-5 cells treated with 5-azacytidine and growth factors (GM-CSF and SCF, according to the schedule presented in FIG. 1) and untreated HS-5 cells were injected into the tail vein of NOD/SCID mice 3 hours after exposure to sub-lethal radiation (30 Gy). Bone marrow cells were harvested 3 weeks after injection and injected to identical NOD/SCID mice 3 hours after exposure to sub-lethal radiation (30 Gy). Bone marrow cells were harvested 3 weeks thereafter, cytocentrifuged and immunohistochemically stained with anti-HLA-ABC antibodies. The left panel shows bone marrow cells harvested from and mouse injected with bone marrow cells from a mouse that was previously injected with untreated HS-5 cells. The middle and the right panels show bone marrow cells harvested from a mice that were injected with bone marrow cells obtained from mice that were previously transplanted with AZA+growth factor-treated HS-5 cells. The HLA-ABC-positive cells are round with big nuclei morphologically different from mouse bone marrow cells.

To validate that a subpopulation of the transformed HS-5 cells carry stem cell capacity, bone marrow cells from mice injected with untreated HS-5 and from mice injected with AZA+growth factor-treated cells were harvested and injected intravenously into identical NOD/SCID mice 3 hours after exposure to sub-lethal radiation (30 Gy). Bone marrow cells were harvested 3 weeks after injection, cytocentrifuged and immunohistochemically stained with anti-HLA-ABC antibodies. FIG. 12 shows that bone marrow cells from mice that were injected with marrow cells of mice that were transplanted with transdifferentiated HS-5 cells, but not those injected with control cells were positive for HLA staining as analyzed by immunohistochemistry. The arrow in the slide shows HLA positive cells. The marrow was taken at 3 weeks post I.V. bone marrow injection. The left panel shows bone marrow cells harvested from a mouse injected marrow cells of a mouse previously injected with untreated HS-5 cells. The right panel and middle panels show bone marrow cells harvested from mice that were injected with marrow cells of a mouse previously injected with AZA+growth factor-treated HS-5 cells. The HLA-ABC-positive cells are round with big nuclei and were morphologically different from mouse bone marrow cells.

Thus, using two different detection systems, the inventors showed that our method of hematopoietic cellular reprogramming gives rise to cells capable of engraftment in vivo. This capability is probably associated with the presence of CD45 positive cells, as evidenced by the fact that the inventors found cells of human origin in mouse bone marrow cavity. This example demonstrates that cells of the present invention may be successfully administered in vivo. Further, this example demonstrates that the methods of the present invention may be used to repopulate an immune system in vivo.

Example 6

Transdifferentiation of Fibroblasts into Endothelial Cells

In the next set of experiments the inventors determined whether fibroblasts could be reprogrammed to generate endothelial cells. To this end, normal human fibroblasts generated from human bone marrow were cultured in the presence of 5-azacytidine (5 ug/ml) with or without epidermal growth factor (EGF) at 10 ng/ml for approximately one week. Then, the cells were analyzed for the expression of two endothelial cell markers; the endothelial progenitor marker CD-133, as well as the expression of vascular endothelial growth factor-2 receptor (VEGFR-2).

Figure 9:
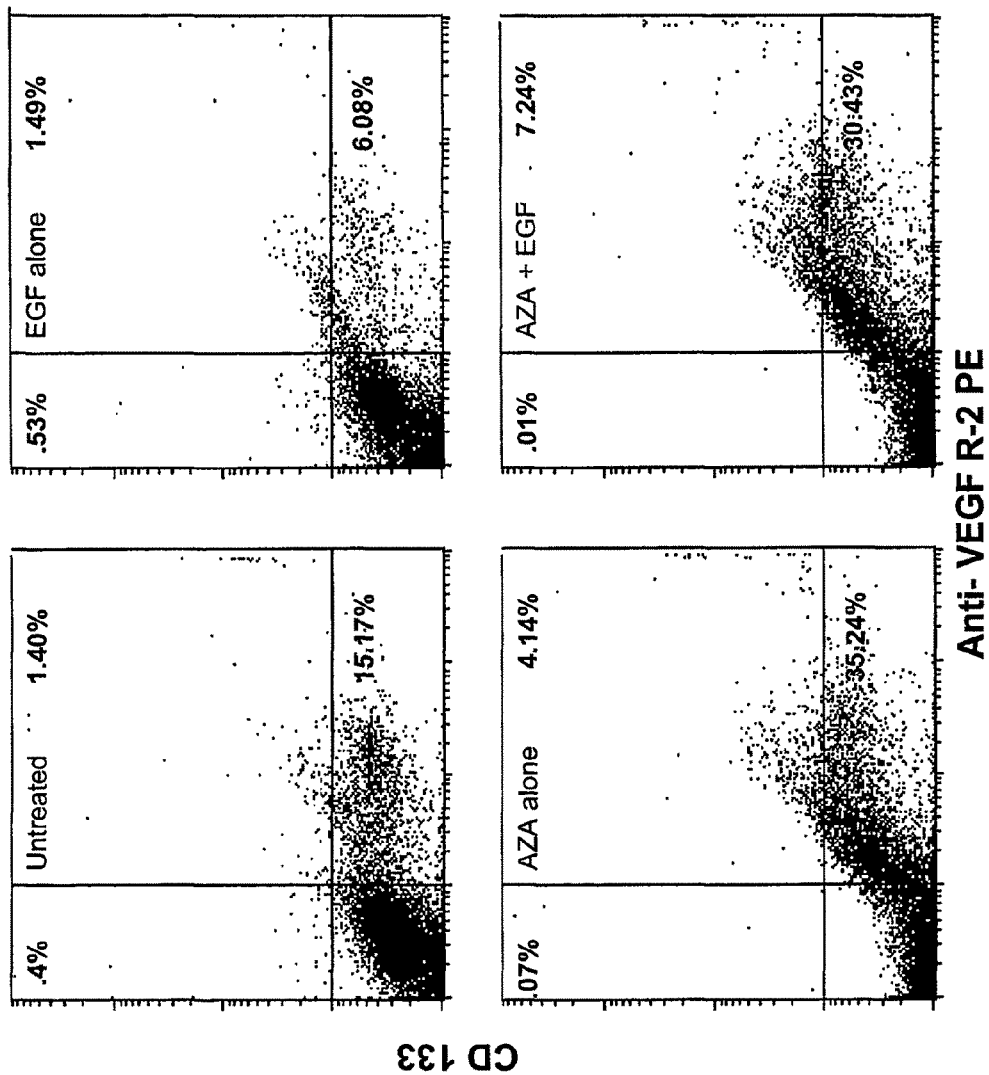
FIG. 9: Conversion of normal human bone marrow stroma to endothelial progenitor cells by 5-azacytidine and endothelial growth factor (EGF). Normal bone marrow-derived CD45-negative MSCs were used in this experiment and Five ng/mL of 5-azacytidine was added to culture on days 1 and 4, and 100 ng/mL EGF were added on days 7 and 10. The cultures were analyzed on day 13. The cells were stained with anti-CD133 APC and anti-VEGFR-2 PE antibodies and analyzed by FACS as described above. The figure shows the cellular distribution and the percent of $CD133^+$, $VEGFR-2^+$, and $CD133^+VEGFR-2^+$ cells of untreated MSCs and 5-azacytidine (AZA)—and/or EGF-treated cells. Note that the when treated with AZA+EGF 7.34% of MSC become $CD133^+VEGFR-2^+$.

In particular, normal bone marrow-derived CD45-negative mesenchymal cells (ie., bone marrow-derived fibroblastic cells) were used in this experiment and five ng/mL of 5-azacytidine was added to culture on days 1 and 4, and 100 ng/ml EGF were added on days 7 and 10. The cultures were analyzed on day 13. The cells were stained with anti-CD133 APC and anti-VEGFR-2 PE antibodies and analyzed by FACS as described above. The results, as seen in FIG. 9, shows the cellular distribution and the percent of $CD133^+$, $VEGFR-2^+$, and $CD133^+VEGFR-2^+$ cells of untreated cells and 5-azacytidine (AZA) and/or EGF-treated cells. Note that the when treated with AZA+EGF 7.34% of bone marrow-derived cells become $CD133^+VEGFR-2^+$. FIG. 9 shows that the percentage of control and EGF-treated cells expressing both CD-133 and VEGFR-2 was insignificant (<1.5%). When cells were exposed to 5-azacytidine a significant portion of the cells expressed both markers (4.14%). Adding EGF to 5-azacytidine treated cells augmented the number of cells expressing both CD133 and VEGFR-2. Similar results were obtained when human foreskin fibroblasts were used.

Example 7

Transdifferentiation of Human Foreskin Fibroblasts into Cells Expressing Both CD45 and CD34

Normal human fibroblasts were treated with the combination of 5-azacytidine and the growth factors GM-CSF and SCF. In particular, human skin fibroblasts were incubated with 5-azacytidine (AZA) and growth factors (50 ng/mL of GM-CSF and 50 ng/mL of SCF). AZA was added to the cultures on days 1, 2, 3, and 4, whereas growth factors were added on days 4 and 5. The cultures were analyzed on day 6. Treated and untreated cells were stained with anti-CD34 PE and anti-CD45 FITC and analyzed by FACS as described above, and the results are shown in FIG. 14. As shown in the upper corner of the right panel, 2.37% of the AZA and growth factor-treated cells were $CD34^+CD45^+$.

Thus, the results show that control treated cells expressed negligible level of both surface markers. In contrast, the method of fibroblast transdifferentiation reprogrammed about 4.4% to become CD45 positive cells. Importantly, out of the total CD45 positive cell population, 53% of cells also expressed the stem cell marker CD34. Therefore, our method is capable of generating cells expressing both CD34 and CD45, the classical expression profile of human hematopoietic stem cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. R. Steinbrook. The cord-blood-bank controversies. N Engl J Med 2004, 351; 2255-7.
2. J. N. Barker and J. E. Wagner. Umbilical cord blood transplantation: current state of the art. Curr Opin Oncol 2002; 14; 160-4.
3. A. J. Friedenstein, R. K. Chailakhyan, N. V. Latsinik, A. F. Panasyuk and I. V. Keiliss-Borok, Stromal cells responsible for transferring the microenvironment of the hemopoietic tissues. Cloning in vitro and retransplantation in vivo, Transplantation 1974, 17; 331-340.
4. A. J. Friedenstein, U. Gorskaja and N. N. Kalugina. Fibroblast precursors in normal and irradiated mouse hematopoietic organs. Exp. Hematol. 1976, 4; 267-274.
5. R. F. Pereira, K. W. Halford, M. D. O'Hara, D. B. Leeper, B. P. Sokolov, M. D. Pollard, O. Bagasra and D. J. Prockop. Cultures of adherent cells from marrow can serve as long-lasting precursor cells for bone, cartilage and lung in irradiated mice, Proc. Natl. Acad. Sci. U.S.A. 1995, 92; 4857-4861
6. M. F. Pittenger, A. M. Mackay, S. C. Beck, R. K. Jaiswal, R. Douglas, J. D. Mosca, M. A. Moorman, D. W. Simonetti, S. Craig and D. R. Marshak. Multilineage potential of adult human mesenchymal stem cells. Science 1999, 284; 143-147
7. I. Sekiya, J. T. Vuoristo, B. L. Larson and D. J. Prockop, In vitro cartilage formation by human adult stem cells from bone marrow stroma defines the sequence of cellular and molecular events during chondrogenesis. Proc. Natl. Acad. Sci. U.S.A. 2002, 49; 4397-4402
8. T. M. Dexter, E. Spooncer, R. Schofield, B. I. Lord and P. Simmons. Haemopoietic stem cells and the problem of self-renewal. Blood Cells 1984, 10:315-339.

9. T. W. Austin, G. P. Solar, F. C. Ziegler, L. Liem and W. Matthews. A role for the Wnt gene family in hematopoiesis: expansion of multilineage progenitor cells. Blood 1997, 89; 3624-3635.
10. D. J. Van Den Berg, A. K. Sharma, E. Bruno and R. Hoffman. Role of members of the Wnt gene family in human hematopoiesis. Blood 1998, 92; 3189-3202.
11. K. Willert, J. D. Brown, E. Danenberg, A. W. Duncan, I. L. Weissman, T. Reya, J. R. Yates III and R. Nusse. Wnt proteins are lipid-modified and can act as stem cell growth factors. Nature 2003, 423; 448-452
12. C. A. Gregory, H. Singh, A. S. Perry and D. J. Prockop. Wnt signaling inhibitor Dkk-1 is required for re-entry into the cell cycle of human adult stem cells from bone marrow stroma (hMSCs). J. Biol. Chem. 2003, 278; 28067-28078.
13. M. Reyes and C. M. Verfaillie. Characterization of multipotent adult progenitor cells, a subpopulation of mesenchymal stem cells. Ann. N. Y. Acad. Sci. 2001, 938; 231-233.
14. Y. Jiang, B. Vaessen, T. Lenvik, M. Blackstad, M. Reyes and C. M. Verfaillie. Multipotent progenitor cells can be isolated from postnatal murine bone marrow, muscle, and brain. Exp. Hematol. 2002, 30; 896-904
15. Y. Jiang, B. N. Jahagirdar, R. L. Reinhardt, R. E. Schwartz, C. D. Keene, X. R. Ortiz-Gonzalez, M. Reyes, T. Lenvik, T. Lund, M. Blackstad, J. Du, S. Aldrich, A. Lisberg, W. Low, D. A. Largaespada and C. M. Verfaillie. Pluripotency of mesenchymal stem cells derived from adult marrow. Nature 2002, 418; 41-49
16. Y. Jiang, D. Henderson, M. Blackstad, A. Chen, R. F. Miller and C. M. Verfaillie. Neuroectodermal differentiation from mouse multipotent adult progenitor cells. Proc. Natl. Acad. Sci. U.S.A. 2003 (Suppl. 1), 100; 118554-118560.
17. D. C. Colter, R. Class, C. M. DiGirolamo and D. J. Prockop. Rapid expansion of recycling stem cells in cultures of plastic-adherent cells from human bone marrow. Proc. Natl. Acad. Sci. U.S.A. 2000, 20; 7294-7299.
18. I. Sekiya, B. L. Larson, J. R. Smith, R. Pochampally, J. G. Cui and D. J. Prockop. Expansion of human adult stem cells from bone marrow stroma: conditions that maximize the yields of early progenitors and evaluate their quality. Stem Cells 2002, 20; 530-541.
19. J. L. Spees, C. A. Gregory, H. Singh, H. A. Tucker, A. Piester, P. J. Lynch, J. Smith and D. J. Prockop. Internalized antigens must be removed to prepare hypo-immunogenic mesenchymal stem cells for cell and gene therapy. Molec. Ther. 2004, 9; 747-756.
20. E. M. Horwitz, D. J. Prockop, L. A. Fitzpatrick, W. W. Koo, P. L. Gordon, M. Neel, M. Sussman, P. Orchard, J. C. Marx, R. E. Pyeritz and M. K. Brenner. Transplantability and therapeutic effects of bone marrow-derived mesenchymal cells in children with osteogenesis imperfecta. Nat. Med. 1999, 5; 309-313.
21. E. M. Horwitz, D. J. Prockop, P. L. Gordon, W. W. Koo, L. A. Fitzpatrick, M. D. Neel, M. E. McCarville, P. J. Orchard, R. E. Pyeritz and M. K. Brenner. Clinical responses to bone marrow transplantation in children with severe osteogenesis imperfecta. Blood 2001, 97; 1227-1231.
22. E. M. Horwitz, P. L. Gordon, W. K. Koo, J. C. Marx, M. D. Neel, R. Y. McNall, L. Muul and T. Hofmann. Isolated allogeneic bone marrow-derived mesenchymal cells engraft and stimulate growth in children with osteogenesis imperfecta: implications for cell therapy of bone. Proc. Natl. Acad. Sci. U.S.A. 2002, 99; 8932-8937.
23. O. N. Koc, J. Day, M. Nieder, S. L. Gerson, H. M. Lazarus and W. Krivit, Allogeneic mesenchymal stem cell infusion for treatment of metachromatic leukodystrophy (MLD) and Hurler syndrome (MPS-IH). Bone Marrow Transplant. 2002, 30; 215-222.
24. A. Angoulvant, Clerc, S. Benchalal, C. Galambrun, A. Farre, Y. Bertrand and A. Eljaafari. Human mesenchymal stem cells suppress induction of cytotoxic response to alloantigens. Biorheology 2004, 41; 469-476.
25. K. Le Blanc. Immunomodulatory effects of fetal and adult mesenchymal stem cells. Cytotherapy 2003, 5; 485-489.
26. K. Le Blanc, C. Tammik, K. Rosendahl, E. Zetterberg and O. Ringden. HLA expression and immunologic properties of differentiated and undifferentiated mesenchymal stem cells. Exp. Hematol. 2003, 31; 890-896.
27. S. M. Devine, C. Cobbs, M. Jennings, A. Bartholomew and R. Hoffman. Mesenchymal stem cells distribute to a wide range of tissues following systemic infusion into nonhuman primates, Blood 2003, 101; 2999-3001
28. A. J. Friedenstein, K. V. Petrakova, A. I. Kurolesova, and G. P. Frolova. Transplantation 1968, 6; 230-247
29. E. A. Olmsted-Davis, Z. Gugala, F. Camargo, F. H. Gannon, K. Jackson, K. A. Kienstra, H. D. Shine, R. W. Lindsey, K. K. Hirschi, M. A. Goodell, M. K. Brenner, and A. R. Davis. Primitive adult hematopoietic stem cells can function as osteoblast precursors. Proc. Natl Acad Sci USA. 2003, 100:15877-82.
30. M. Körbling, and Z. Estrov. Adult stem cells for tissue repair—a new therapeutic concept? N Engl J Med. 2003; 349:570-82
31. B. Hennessy, M. Körbling, and Z. Estrov. Circulating stem cells and tissue repair. Panminerva Med. 2004; 46:1-11
32. R. Holliday. The inheritance of epigenetic defects. Nature 1942; 150:563-565
33. I. Wilmut, N. Beaujean, P. A. de Sousa, A. Dinnyes, T. J. King, L. A. Paterson, D. N. Wells, and L. E. Young. Somatic cell nuclear transfer. Nature 2002; 419:583-586
34. G. Egger, G. Liang, A. Aparicio, and P. A. Jones. Epigenetics in human disease and prospects for epigenetic therapy. Nature 2004; 429:457-463
35. V. Santini, H. M. kantarjian, and J. P. Issa. Canges in DNA methylation in neoplasia: pathophysiology and therapeutic implications. Ann. Intern. Med. 2001; 134:573-586
36. J. P. Issa. CpG island methylation in cancer. Nat Rev Cancer 2004; 4:988-993
37. J. P. Issa. Decitabine. Curr opin Oncol, 2003; 15:446-451
38. P. A. Zuk, M. Zhu, P. Ashjian, D. A. De Ugarte, J. I. Huang, H. Mizuno, Z. C. Alfonso, J. K. Fraser, P. Benhaim and M. H. Hedrick, Human adipose tissue is a source of multipotent stem cells, Mol. Biol. Cell. 2002, 13; 4279-4295.
39. M. W. Lee, J. Choi, M. S. Yang, Y. J. Moon, J. S. Park, H. C. Kim and Y. J. Kim, Mesenchymal stem cells from cryopreserved human umbilical cord blood, Biochem. Biophys. Res. Commun. 2004, 320; 273-278
40. P. S. Anker, S. A. Scherjon, C. Kleijburg-van der Keur, G. M. de Groot-Swings, F. H. Claas, W. E. Fibbe and H. H. Kanhai, Isolation of mesenchymal stem cells of fetal or maternal origin from human placenta, Stem Cells 2004, 22; 1338-1345
41. B. L. Yen, H. I. Huang, C. C. Chien, H. Y. Jui, B. S. Ko, M. Yao, C. T. Shun, M. L. Yen, M. C. Lee and Y. C. Chen, Isolation of multipotent cells from human term placenta, Stem Cells 2005, 23; 3-9
42. M. Miura, S. Gronthos, M. Zhao, B. Lu, L. W. Fisher, P. G. Robey and S. Shi, SHED: stem cells from human exfoliated deciduous teeth, Proc. Natl. Acad. Sci. U.S.A. 2003, 100; 5807-5812 43. Toma J G, Akhavan M, Fernandes K J, Barnabe-Heider F, Sadikot A, Kaplan D R, Miller F D.

Isolation of multipotent adult stem cells from the dermis of mammalian skin. Nat Cell Biol. 2001; 3:778-84;

44. K. J. Fernandes, I. A. McKenzie, P. Mill, K. M. Smith, M. Akhavan, F. Barnabe-Heider, J. Biernaskie, A. Junek, N. R. Kobayashi, J. G. Toma, D. R. Kaplan, P. A. Labosky, V. Rafuse, C. C. Hui, and F. D. Miller. A dermal niche for multipotent adult skin-derived precursor cells. Nat Cell Biol 2004; 6:1082-1093

45 J. G. Toma, I. A. McKenzie, D. Bagli, F. D. Miller. Isolation and characterization of multipotent skin-derived precursors from human skin. Stem Cells. 2005; 23:727-37

46. G. Bartsch, J. J. Yoo, P. De Coppi, M. M. Siddiqui, G. Schuch, H. G. Pohl, J. Fuhr, L. Perin, S. Soker, and A. Atala. Propagation, expansion, and multilineage differentiation of human somatic stem cells from dermal progenitors. Stem cells Dev 2005; 14:337-348

47. G. Rawadi, B. Vayssiere, F. Dunn, R. Baron and S. Roman-Roman, BMP2 controls alkaline phosphatase expression and osteoblast mineralization by a Wnt autocrine loop, J. Bone Miner. Res. 2003, 18; 1842-1853.

48. M. Habib, F. Fares, C. A. Bourgeois, C. Bella, J. Bernardino, F. Hemandez-Blazquez, A. de Capoa, and A. Neveleau. DNA global hypomethylation in EBV-transformed interphase nuclei. Exp Cell Res 1999; 249:46-53

49. A. Ferrajoli, M. Talpaz, R. Kurzrock, and Z. Estrov. Analysis of the effects of tumor necrosis factor inhibitors on human hematopoiesis. Stem Cells 11: 112-119, 1993.

50. S. Milotinovic, Q. Zhuan, A. Niveleau, and M. Szyf. Epigenomic stress response. Knockdown of DNA methyltransferase 1 triggers an intra-S-phase arrest of DNA replication and induction of stress response genes. J. Biol. Chem., 278: 14985-95, 2003

The invention claimed is:

1. A method of transdifferentiating fibroblasts of a bone marrow stromal cell into hematopoietic cells, the method comprising culturing said fibroblasts in a medium comprising a demethylating agent, granulocyte-macrophage stimulating factor (GM-CSF) and stem cell factor (SCF) in an amount and for a time effective to transdifferentiate said cells into hematopoietic cells, to provide a population of cells comprising said hematopoietic cells.

2. The method of claim 1, wherein the demethylating agent is 5-azacytidine or 5-aza-2-deoxycytidine, zebularine, procaine, epigallocatechin-3-gallate, RG108, 1-β-D-arabinofuranosyl-5-azacytosine, dihydro-5-azacytidine or L-ethionine.

3. The method of claim 2, wherein the demethylating agent is 5-azacytidine or 5-aza-2-deoxycytidine.

4. The method of claim 1, wherein the cells are cultured in the medium comprising the demethylating agent for a period of time of from about 1 minute to about 1 week.

5. The method of claim 1, wherein the demethylating agent is present in the medium at from about 0.1 µg/ml to about 10 µg/ml.

6. The method of claim 1, further comprising administering cells of the cell population to a subject.

7. The method of claim 6, wherein the subject is a human subject.

* * * * *

UNITED STATES PATENT AND TRADEMARK OFFICE
CERTIFICATE OF CORRECTION

| | | |
|---|---|---|
| PATENT NO. | : 8,440,460 B2 | Page 1 of 1 |
| APPLICATION NO. | : 11/996732 | |
| DATED | : May 14, 2013 | |
| INVENTOR(S) | : Estrov et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1508 days.

Signed and Sealed this
Thirtieth Day of September, 2014

Michelle K. Lee
*Deputy Director of the United States Patent and Trademark Office*